US005840687A

United States Patent [19]
Harkins et al.

[11] Patent Number: 5,840,687
[45] Date of Patent: Nov. 24, 1998

[54] MODIFIED LIGANDS FOR RECEPTOR TYROSINE KINASES

[75] Inventors: Richard N. Harkins, Alameda; Marian Seto, South San Francisco; Bradley A. Katz, San Francisco, all of Calif.

[73] Assignee: Schering Aktiengesellschaft, Berlin, Germany

[21] Appl. No.: 384,714

[22] Filed: Feb. 2, 1995

[51] Int. Cl.$^6$ ..................................................... C12P 21/02
[52] U.S. Cl. ........................... 514/12; 435/244; 930/120; 530/323; 530/324
[58] Field of Search .............................. 514/12; 435/244; 930/120; 530/323, 324

[56] References Cited

U.S. PATENT DOCUMENTS 5,589,356  12/1996  Tam ......................................... 530/323

FOREIGN PATENT DOCUMENTS

WO91/01141  2/1991  WIPO .

OTHER PUBLICATIONS

Bahr et al., "Antigenic properties of the second loop of transforming growth factor–α by synthetic peptides", *Acta Chemical Scandinavica* (1992) 46:266–270.

Tam et al. "Efficient approach to synthesis of two–chain asynetric cysteine analogs of receptor–binding region of transforming growth factor–α", *Int. J. of Peptide and Protein Res.* (1992) 39:464–47.

Brown et al., "Polypeptide" (May 9, 1986), Chem Abs #4 Plus Abs #1987: 114294.

Carpenter, G. "Receptors for Epidermal Growth Factor and Other Polypeptide Mitogens," *Ann. Rev. Biochem*, (1987) 56:881–914.

Kimball, E. et al. "Epidermal Growth Factor (EGF) Binding to Membranes Immoblized in Microtiter Wells and Estimation of EGF–Related Transforming Growth Factor Activity", *Biochimica et Biophysica Acta*, (1984) 771:82–88.

DeLarco, J. et al. "Growth factors from murine sarcoma virus–transformed cells", *Proc. Natl. Acad. Sci. USA*, (1978) 75(8):4001–4005.

Hung, M–C, "The neu Proto–oncogene and Breast Cancer", *The Cancer Bulletin*, (1988) 40(5):300–303.

Cohen, S. et al. "Human Epidermal Growth Factor: Isolation and Chemical and Biological Properties", *Proc. Nat. Acad. Sci. USA*, (1975) 72(4):1317–1321.

Winkler, M. et al., "The Purification of Fully Active Recombinant Transforming Growth Factor a Produced in *Escherichia coli*", *The Journal of Biological Chemistry*, (1986) 261 (29):13838–13843.

Marquardt, H. et al., "Transforming growth factors produced by retrovirus–transformed rodent fibroblasts and human melanoma cells: Amino acid sequence homology with epidermal growth factor", *Proc. Natl. Acad. Sci. USA*, (1983) 80:4684–4688.

Janssen, J. et al., "A novel putative tyrosine kinase receptor with oncogenic potential", *Oncogene*, (1991) 6:2113–2120.

Zhang, X. et al., "Amplification and rearrangement of c–erb proto–oncogenes in cancer of human female genital tract", *Oncogene*, (1989) 4:985–989.

O'Bryan, J. et al., "axl , a Transforming Gene Isolated from Primary Human Myeloid Leukemia Cells, Encodes a Novel Receptor Tyrosine Kinase", *Molecular and Cellular Biology*, (1991) 11(10):5016–5031.

Slamon, D. et al., "Studies of the HER–2/ neu Proto–oncogene in Human Breast and Ovarian Cancer", *Science*, (1989) 244:707–712.

Slamon, D. et al., "Human Breast Cancer: Correlation of Relapse and Survival with Amplification of the HER–2/ neu Oncogene", *Science*, (1987)235:177–182.

Martin–Zanca, D., et al., "A human oncogene formed by the fusion of truncated tropomyosin and protein tyrosine kinase sequences", *Nature*, (1986) 319:743–748.

Wilks, A., "Protein Tyrosine Kinase Growth Factor Receptors and Their Ligands in Development, Differentiation, and Cancer", *Advances in Cancer Research*, (1993) 60:43–73.

Spear, K. et al., "Chemical Synthesis of Human Transforming Growth Factor–α", *Techniques in Protein Chemistry II*, (1991) 233–240.

Ullrich, A. et al., "Signal Transduction by Receptors with Tyrosine Kinase Activity"; *Cell*, (1990) 61:203–212.

*Primary Examiner*—Cecilia J. Tsang
*Assistant Examiner*—Patrick R. Delaney
*Attorney, Agent, or Firm*—Wendy L. Washtien

[57] ABSTRACT

The invention provides for synthetic ligands that bind to class I receptor tyrosine kinases. The ligands are analogous in structure to naturally occurring ligands. The modified ligands however, have eliminated the mid-sequence (B) domain present in the native ligands and replaced it with a peptide bridge which links the amino (A) and carboxy (C) domains.

**25 Claims, 5 Dr

Domain Structure of the Receptor Tyrosine Kinase Ligand, TGFα

Domain Structure of Modified Receptor Tyrosine Kinase Ligands

Cys2 = $AA_1$-6
Cys4 = $AA_3$-1
Cys5 = $AA_3$-3
Cys6 = $AA_3$-12

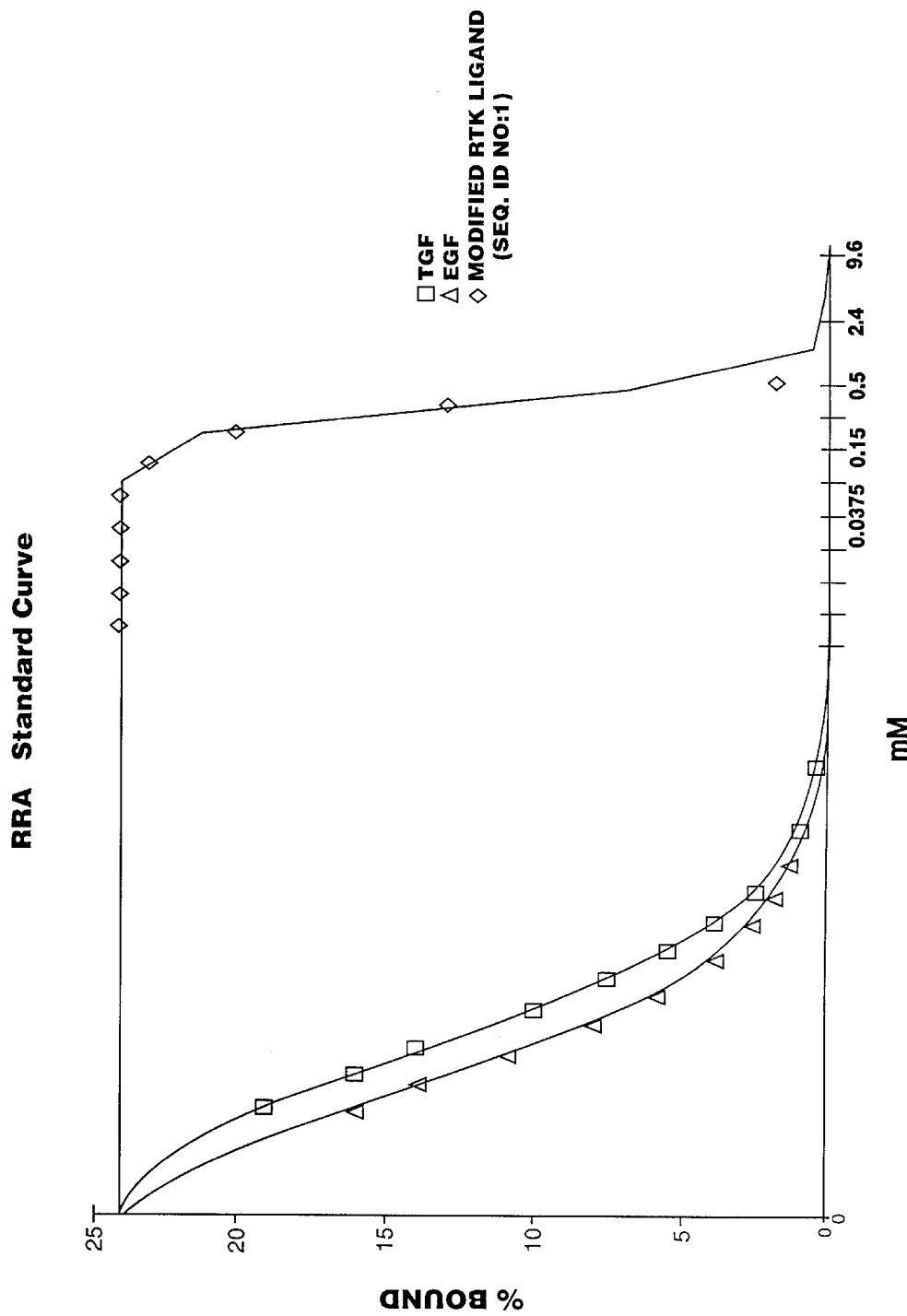

Figure 4A
Class I Receptor Tyrosine Kinase Ligands

| EGF Receptor Ligands | | | | | | | | | | 10 | | | | | | | | | | 20 | | | | | | | | | | 30 | | | | | | | | | | 40 | | | | | | | | | | 50 | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hAR | N | R | K | K | K | N | P | C | N | A | E | F | Q | N | F | C | I | H | G | E | - | - | C | K | Y | I | E | H | L | - | - | E | A | V | T | C | K | Q | Q | E | Y | F | G | E | R | C | G | E | K | S | M | K | T | H | S | M | I |
| rSDG | R | K | K | K | K | N | P | C | A | A | K | F | Q | N | F | C | I | I | G | E | - | - | C | R | Y | I | E | N | L | - | - | E | V | V | T | C | H | Q | D | Y | F | G | E | R | C | G | E | K | T | M | K | T | Q | K | K | D |
| hHB-EGF | L | G | K | K | R | D | P | C | L | R | K | Y | K | D | F | C | I | H | G | E | - | - | R | A | P | S | C | I | - | - | C | H | P | G | Y | H | G | E | R | C | H | G | L | S | L | P | V | E | N | R | L |
| hTGFalpha | V | V | S | H | F | N | D | C | P | D | S | H | T | Q | F | C | F | H | G | T | - | - | C | R | F | L | V | Q | E | - | - | D | K | P | A | C | V | C | H | S | G | Y | V | G | A | R | C | E | H | A | D | L | L | A |
| rTGFalpha | V | V | S | H | F | N | K | C | P | D | S | H | T | Q | Y | C | F | H | G | T | - | - | C | R | F | L | V | Q | E | - | - | E | K | P | A | C | V | C | H | S | G | Y | V | G | V | R | C | E | H | A | D | L | L | A |
| mBetacellulin | V | K | T | H | F | S | R | C | P | K | Q | Y | K | H | Y | C | I | H | G | R | - | - | C | R | F | V | V | D | E | - | - | Q | T | P | S | C | I | C | E | K | G | Y | F | G | A | R | C | E | R | V | D | L | F | Y | |
| hEGF | N | S | D | S | E | C | P | L | S | H | D | G | Y | C | L | H | D | G | V | - | - | C | M | Y | I | E | A | L | - | - | D | K | Y | A | C | N | C | V | V | G | Y | I | G | E | R | C | Q | Y | R | D | L | K | W | E | L | R |
| mEGF | N | S | Y | P | G | C | P | S | S | Y | D | G | Y | C | L | N | G | G | V | - | - | C | M | H | I | E | S | L | - | - | D | K | Y | A | C | N | C | V | V | G | Y | S | G | D | R | C | Q | T | R | D | L | R | W | E | L | R |
| rEGF | N | S | N | T | G | C | P | S | S | Y | D | G | Y | C | L | N | G | G | V | - | - | C | M | Y | V | E | S | L | - | - | D | K | Y | A | C | N | C | V | V | G | Y | I | G | E | R | C | Q | H | R | D | L | R | W | | |
| gpEGF | Q | D | A | P | G | C | P | P | S | H | D | G | Y | C | L | H | G | G | V | - | - | C | M | H | I | E | S | L | - | - | D | K | Y | A | C | N | C | V | V | G | Y | V | G | E | R | C | E | H | Q | D | L | D | W | E | | |
| VGF | D | I | P | A | I | R | L | C | G | P | E | G | D | G | Y | C | L | H | G | D | - | - | C | I | H | A | R | D | L | - | - | D | G | M | Y | C | R | C | S | H | G | Y | T | G | I | R | C | Q | H | V | V | L | V | D | Y | Q | R | S |
| SFGF | I | V | K | H | V | K | V | C | N | H | D | Y | E | N | Y | C | L | N | N | G | T | - | C | F | T | I | A | L | D | N | V | S | I | T | P | F | C | V | C | R | I | N | Y | E | G | S | R | C | Q | F | I | N | L | V | T | Y | | |
| vMGF | I | I | K | R | I | K | L | C | N | D | D | Y | K | N | Y | C | L | N | N | G | T | - | C | F | T | V | A | L | N | N | V | S | L | N | P | F | C | A | C | H | I | N | Y | V | G | S | R | C | Q | F | I | N | L | I | T | K | | |

X1 — X2A — X3

EGF-rLigands hAR     human Amphiregulin
rSDG     rat Schwannoma derived growth factor
hHB-EGF     human Heparin binding-EGF
hTGFα(r)     human Transforming growth factor α, (rat)
hEGF (m, r, gp)     human Epidermal growth factor, (murine, rat, guinea pig)

VGF     Vaccinia growth factor (viral)
SFGF     Shopes fibroma growth factor (viral)
vMGF     Myxoma growth factor (viral)

Figure 4B
Class I Receptor Tyrosine Kinase Ligands

| Additional HER Ligands | 1 | | | | | | | | | 10 | | | | | | | | | | 20 | | | | | | | | | 30 | | | | | | | | | 40 | | | | | | | | | 50 | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| hHRG alpha | G | T | S | H | L | V | K | C | A | E | K | E | K | T | F | C | V | N | G | G | E | C | F | M | V | K | D | L | S | N | P | S | R | Y | L | C | K | C | Q | P | G | F | T | G | A | R | C | T | E | N | V | P | M | K | V | Q | N | Q |
| rNDF | G | T | S | H | L | I | K | C | A | E | K | E | K | T | F | C | V | N | G | G | E | C | F | T | V | K | D | L | S | N | P | S | R | Y | L | C | K | C | Q | P | G | F | T | G | A | R | C | T | E | N | V | P | M | K | V | Q | T | Q |
| hHRG beta 1 | G | T | S | H | L | V | K | C | A | E | K | E | K | T | F | C | V | N | G | G | E | C | F | M | V | K | D | L | S | N | P | S | R | Y | L | C | K | C | P | N | E | F | T | G | D | R | C | Q | N | Y | V | M | A | S | F | Y | K | H |
| hHRG beta 2 | G | T | S | H | L | V | K | C | A | E | K | E | K | T | F | C | V | N | G | G | E | C | F | M | V | K | D | L | S | N | P | S | R | Y | L | C | K | C | P | N | E | F | T | G | D | R | C | Q | N | Y | V | M | A | S | F | Y | K | - |
| hHRG beta 3 | G | T | S | H | L | V | K | C | A | E | K | E | K | T | F | C | V | N | G | G | E | C | F | M | V | K | D | L | S | N | P | S | R | Y | L | C | K | C | P | N | E | F | T | G | D | R | C | Q | N | Y | V | M | A | S | F | Y | S | T |
| hGGF | G | T | S | H | L | V | K | C | A | E | K | E | K | T | F | C | V | N | G | G | E | C | F | M | V | K | D | L | S | N | P | S | R | Y | L | C | K | C | P | N | E | F | T | G | D | R | C | Q | N | Y | V | M | A | S | F | Y | S | T |
| cARIA | G | T | S | H | L | T | K | C | D | I | K | Q | K | A | F | C | V | N | G | G | E | C | F | M | V | K | D | L | P | N | P | P | R | Y | L | C | R | C | P | N | E | F | T | G | N | R | C | Q | N | Y | V | M | A | S | F | Y | K | H |
| rASGP2-EGF1 | E | F | C | Q | N | H | S | C | P | - | - | - | - | - | - | C | Y | N | H | G | H | C | D | I | S | G | P | - | - | - | - | P | D | C | Q | P | T | C | A | P | A | F | T | G | N | R | C | F | L | A | G | N | N | F | T | P | I |
| rASGP2-EGF2 | G | V | T | C | V | S | P | C | S | - | - | - | - | - | - | C | E | G | Y | C | Y | C | K | H | L | - | - | - | - | - | - | P | D | G | P | Q | C | T | C | A | T | F | S | I | G | E | R | C | E | H | L | S | V | K | | | |
| CRIPTO | S | K | E | L | N | R | T | C | - | - | - | - | - | - | - | C | L | N | G | G | T | C | - | - | - | - | - | - | - | - | - | M | L | G | S | F | C | A | C | P | P | S | F | Y | G | R | N | C | E | H | D | V | R | K | E | N | C | G | S |

Additional HER Ligands hHRGα, HRG β1, β2, β3    human Heregulin α, β1, β2, β3
rNDF                      rat Neu differentiation factor
hGGF                      human Glial growth factor
cARIA                     chicken Acetycholine receptor
                          inducing activity
rASPG2                    rat Asialoproteoglycan 2

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Ser  His  Thr  Gln  Phe  Cys  Phe  His  Gly  Thr  Gly  Cys  Val  Cys  His  Ser
1                   5                        10                       15

Gly  Tyr  Val  Gly  Ala  Arg  Cys  Glu  His  Ala  Asp  Leu  Leu  Ala
                    20                       25                       30
```

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser  His  Thr  Gln  Phe  Cys  Phe  His  Gly  Thr  Ser  Cys  Val  Cys  His  Ser
1                   5                        10                       15

Gly  Tyr  Val  Gly  Ala  Arg  Cys  Glu  His  Ala  Asp  Leu  Leu  Ala
                    20                       25                       30
```

( 2 ) INFORMATION FOR SEQ ID NO:3:

( i ) SEQUENCE CHARACTERISTICS:
        ( A ) LENGTH: 31 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Ser  His  Thr  Gln  Phe  Cys  Phe  His  Gly  Thr  Pro  Gly  Cys  Val  Cys  His
1                   5                        10                       15

Ser  Gly  Tyr  Val  Gly  Ala  Arg  Cys  Glu  His  Ala  Asp  Leu  Leu  Ala
```

|  | 20 | 25 | 30 |
|---|---|---|---|

(2) INFORMATION FOR SEQ ID NO:4:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:4:

```
Ser His Thr Gln Phe Cys Phe His Gly Thr Ser Pro Gly Cys Val Cys
 1               5                  10                  15
His Ser Gly Tyr Val Gly Ala Arg Cys Glu His Ala Asp Leu Leu Ala
            20                  25                  30
```

(2) INFORMATION FOR SEQ ID NO:5:

(i) SEQUENCE CHARACTERISTICS:
        (A) LENGTH: 32 amino acids
        (B) TYPE: amino acid
        (D) TOPOLOGY: linear (ii) MOLECULE TYPE: protein (xi) SEQUENCE DESCRIPTION: SEQ ID NO:5:

```
Ser His Thr Gln Phe Cys Phe His Gly Thr Ser Pro Asn Cys Val Cys
 1               5                  10                  15
His Ser Gly Tyr Val Gly Ala Arg Cys Glu His Ala Asp Leu Leu Ala
            20                  25                  30
```

(2) INFORMATION FOR SEQ ID NO:6:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:6:

```
Lys Gly Lys Thr Phe Cys Val Asn Gly Gly Glu Gly Cys Lys Cys Gln
 1               5                  10                  15
Pro Gly Phe Thr Gly Ala Arg Cys Thr Glu Asn Val Pro Met Lys
            20                  25                  30
```

(2) INFORMATION FOR SEQ ID NO:7:

(i) SEQUENCE CHARACTERISTICS:
        (A) LENGTH: 31 amino acids
        (B) TYPE: amino acid
        (D) TOPOLOGY: linear (ii) MOLECULE TYPE: protein (xi) SEQUENCE DESCRIPTION: SEQ ID NO:7:

```
Lys Gly Lys Thr Phe Cys Val Asn Gly Gly Glu Ser Cys Lys Cys Gln
 1               5                  10                  15
Pro Gly Phe Thr Gly Ala Arg Cys Thr Glu Asn Val Pro Met Lys
            20                  25                  30
```

(2) INFORMATION FOR SEQ ID NO:8:

(i) SEQUENCE CHARACTERISTICS:
        (A) LENGTH: 32 amino acids
        (B) TYPE: amino acid (D) TOPOLOGY: linear (ii) MOLECULE TYPE: protein (xi) SEQUENCE DESCRIPTION: SEQ ID NO:8:

```
Lys Gly Lys Thr Phe Cys Val Asn Gly Gly Glu Pro Gly Cys Lys Cys
1               5                   10                  15
Gln Pro Gly Phe Thr Gly Ala Arg Cys Thr Glu Asn Val Pro Met Lys
            20                  25                  30
```

(2) INFORMATION FOR SEQ ID NO:9:

(i) SEQUENCE CHARACTERISTICS:
(A) LENGTH: 33 amino acids
(B) TYPE: amino acid
(D) TOPOLOGY: linear (ii) MOLECULE TYPE: protein (xi) SEQUENCE DESCRIPTION: SEQ ID NO:9:

```
Lys Gly Lys Thr Phe Cys Val Asn Gly Gly Glu Ser Pro Gly Cys Lys
1               5                   10                  15
Cys Gln Pro Gly Phe Thr Gly Ala Arg Cys Thr Glu Asn Val Pro Met
                20                  25                  30
Lys
```

(2) INFORMATION FOR SEQ ID NO:10:

(i) SEQUENCE CHARACTERISTICS:
(A) LENGTH: 33 amino acids
(B) TYPE: amino acid
(D) TOPOLOGY: linear (ii) MOLECULE TYPE: protein (xi) SEQUENCE DESCRIPTION: SEQ ID NO:10:

```
Lys Gly Lys Thr Phe Cys Val Asn Gly Gly Glu Ser Pro Asn Cys Lys
1               5                   10                  15
Cys Gln Pro Gly Phe Thr Gly Ala Arg Cys Thr Glu Asn Val Pro Met
                20                  25                  30
Lys
```

MODIFIED LIGANDS FOR RECEPTOR TYROSINE KINASES

FIELD OF THE INVENTION

This invention provides compounds which are analogs of native ligands for receptor tyrosine kinases. These analogs will bind receptor tyrosine kinases and may be used either to inhibit the activity of native ligands or to activate the receptor in the absence of native ligands.

BACKGROUND OF THE INVENTION

Polypeptides such as growth factors, differentiation factors, and hormones are crucial components of the regulatory system that coordinates the development of multicellular organisms. Many of these factors mediate their actions by binding to and activating cell surface receptors that have an intrinsic tyrosine kinase activity (i.e. that phosphorylate tyrosine residues on intracellular polypeptides when bound and activated by a ligand).

Cell surface receptors with tyrosine kinase activity, known as receptor tyrosine kinases (RTKs), have characteristic molecular topologies. RTKs, in general, are characterized by an extracellular ligand-binding domain, a single transmembrane domain, a single tyrosine kinase domain, and at least one regulatory domain which serves to regulate the catalytic activity of the kinase function of the RTK. On the basis of sequence similarity and distinct structural characteristics, it is possible to further divide these receptors into various classes. RTKs of the group known as Class I are, in particular, characterized by the presence of two cysteine-rich sequence repeat regions within the extracellular domains of these receptors. Included within the Class I receptors are EGF, DER, let23, HER2/c-erbB-2/neu, HER3/c-erbB-3, HER4/c-erbB-4, and Xmrk.

Class I RTKs mediate the interaction of cells with numerous growth factors including transforming growth factor (TGF-α), epidermal growth factor (EGF), and heregulin. These receptors are widely distributed throughout different tissues and, depending on cell type and physiological circumstances, act to mediate growth inhibition or induction of cell proliferation and differentiation.

The ligands which bind Class I RTKs (e.g. TGF-α, EGF, heregulin) are a highly conserved group of polypeptides (see FIGS. 4A and 4B). Cellular response to these ligands, however, is highly variable, depending on the ligand, the RTK activated, the target tissue, and the developmental stage of the tissue when it is exposed to the ligand.

Although not well understood, RTK/ligand interactions appear to have major roles in the induction events that mediate important developmental processes such as the differentiation of germ layers in the developing embryo (Wilks, Adv. Cancer. Res., 60: 43–73 (1993)).

The EGF receptor, a well-known Class I RTK, is detectable on a large variety of cell types or tissues, one exception being hemopoietic cells. Evidence indicates that the EGF receptor mediates the biological signals not only of EGF, but also of other EGF-like growth factors, such as transforming growth factor alpha (TGF-α) and the vaccinia virus growth factor (VGF) (Carpenter, Ann. Rev. Biochem., 56: 881–914 (1987)), as well as others indicated in FIG. 4A. Activation of the EGF receptor has been shown to enhance cellular proliferation (Id).

In addition to proliferation and differentiation, RTKs are associated with the etiology of various cancers. In cancerous conditions, RTKs are often over-expressed (Slamon et al., Science, 235: 177–182 (1987); Slamon et al., Science, 244: 707–712 (1989); Hung, Cancer Bull., 40: 300–303 (1988); Zhang et al., Oncogene, 4: 985–989 (1989)) and/or inappropriately expressed (Janssen et al., Oncogene, 6: 2113–2120 (1991); O'Bryan et al., Mol. Cell. Biol., 11: 5016–5031 (1991)) or expressed in a ligand-independent activated form (Martin-Zanca et al., Nature, 319: 743–748 (1986)). Over expression or altered expression of the EGF receptor has been reported for a variety of human tumor (carcinoma) tissues including breast, liver, bladder, pancreas, glioblastomas, sarcomas, lung, and most frequently for squamous carcinomas (Carpenter, Ann. Rev. Biochem., 56: 881–914 (1987)).

Similarly, amplification of another growth factor, HER2/neu, has been correlated with the etiology of breast cancer (Slamon et. al., Science, 244: 707–712 (1989)). Numerous studies have shown that patients found to have multiple copies of the HER2/neu gene in DNA taken from their tumors had a shorter time to relapse as well as a shorter overall survival rate, indicating that amplification of the gene for the HER2/neu receptor was prognostic for disease behavior in these individuals (Id at 707).

The compounds of the present invention are modified RTK ligands which specifically bind to Class I RTKs. The modified RTK ligands of the present invention are generally analogous to native RTK ligands, but have modifications which eliminate nonessential regions of the polypeptide. The modified RTK ligands are thus shorter than native RTK ligands and therefore easier to synthesize chemically. The modifications may also alter the activity of the ligand. Thus, the modified RTK ligands may possess either an agonist or an antagonistic biological activity.

When the modified RTK ligands are labelled they may be useful as probes to assay for the presence, absence, or over-expression of RTKs. As receptor over-expression is associated with cancer etiology, use of labelled modified RTK ligands may provide an assay useful both in research and in a clinical context.

In addition, the modified RTK ligands of the present invention may bind RTKs without activating them. They may therefore be used as competitive inhibitors to block the activation of the receptors in vitro or in vivo. The modified RTK ligands are thus powerful tools both for investigation of the biology of RTKs and as potential therapeutics in the treatment of disorders associated with the over-expression of RTKs.

While many RTKs have been identified, the identification of corresponding ligands for some RTKs has lagged far behind (Wilks, Adv. Cancer Res., 60: 43–73 (1993)). The lack of a specific ligand to activate a particular receptor makes it difficult to study the biological function of that receptor. The modified RTK ligands of the present invention may be used to activate or inhibit receptors whose native ligand is unknown. This may aid in the identification of the biological activities of a particular receptor and consequently the identification of the corresponding native ligand.

SUMMARY OF THE INVENTION

The present invention provides modified ligands specific for Class I RTKs. The modified RTK ligands may have agonistic or antagonistic activities. Further, they may easily be labelled to provide a rapid assay for the presence or absence of RTKs on particular cells.

Accordingly, this invention is directed to modified RTK ligands having specificity for a Class I RTK and corresponding to a native RTK ligand having amino acids forming three cysteine linkages, said linkages numbered in ascending order with regard to the relative position of their first cysteine with respect to the amino terminus of the native RTK ligand:

wherein the first, second, and third cysteine linkages of the native RTK ligand define a domain A, a domain B and a domain C, and the three linkages comprise a first, a second, a third, a fourth, a fifth and a sixth cysteine, with the first linkage being between the first and third cysteine, the second linkage being between the second and fourth cysteine, and the third linkage being between the fifth and sixth cysteine; where domain A is defined as the first cysteine, those amino acids situated between the first and the second cysteines, and the second cysteine; domain B is defined as those amino acids situated between the second and fourth cysteines; and domain C is defined as the fourth cysteine and those amino acids attached to the carboxy terminus of the fourth cysteine; and, of the fourth cysteine; and, wherein the modified RTK ligand has four cysteine amino acids forming two linkages between cysteines two and four, and five and six, respectively, and having two domains, $A_1$ and $C_1$ corresponding to domains A and C of the native RTK ligand;

wherein domain $A_1$ consists essentially of the biologically active amino acid sequences of the domain A of a native RTK ligand; and, wherein domain $C_1$ consists essentially of the biologically active amino acid sequences of the domain C of a native RTK ligand; and, wherein cysteine two, which is the carboxy terminus of domain $A_1$, and cysteine four, which is the amino terminus of domain $C_1$, are connected by a peptide bridge comprising a prebridge subdomain and a bridge subdomain, and where, within the peptide bridge, there is a β-turn corresponding to the β-turn present within domain B of the native RTK ligand.

Another aspect of the invention provides a method for quantifying the presence of receptor tyrosine kinases on cells using labelled modified RTK ligands in a specific binding assay.

A third aspect of the invention is directed toward the treatment of malignancy or aberrant expression which comprises administering to a patient in need thereof a therapeutically effective amount of a modified RTK ligand.

DETAILED DESCRIPTION OF THE INVENTION

Definitions

As used herein, the following terms and phrases, unless otherwise noted, have the meaning indicated:

The term "native RTK ligand" refers to a naturally occurring molecule which binds to a protein with tyrosine kinase activity, typically a receptor on a cell surface. In general, ligands bind specifically to particular proteins. However, it is not required that they do so.

The term "modified RTK ligand" refers to a ligand which has been altered by the addition, elimination, or substitution of one or more amino acid residues normally found in the native RTK ligand. The term modified RTK ligand also includes modifications wherein the side groups of particular amino acid residues are chemically modified or replaced. Modified RTK ligands may be synthesized de novo and do not necessarily require the actual modification of a preexisting native RTK ligand.

The phrase "specifically bind(s)" refers to the binding of a ligand to a particular molecule and to no other molecule to which the ligand is normally exposed in the organism.

The term "residue" refers to an amino acid that is incorporated into a peptide. The amino acid may be a naturally occurring amino acid and, unless otherwise limited, may encompass known analogs of natural amino acids that can function in a similar manner as naturally occurring amino acids. For purposes of this disclosure, amino acid residues are designated herein by their accepted three-letter or one-letter abbreviation, or by the notation "AA", which signifies the presence of an amino acid residue. The amino acids referred to herein are described by shorthand designations as follows:

TABLE 1

Amino Acid Nomenclature

| Name | 3-letter | 1 letter |
|---|---|---|
| Alanine | Ala | A |
| Arginine | Arg | R |
| Asparagine | Asn | N |
| Aspartic Acid | Asp | D |
| Cysteine | Cys | C |
| Glutamic Acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The terms "peptides" and "polypeptides" refer to chains of amino acids whose α carbons are linked through peptide bonds formed by a condensation reaction between the α carbon carboxyl group of one amino acid and the amino group of another amino acid. The terminal amino acid at one end of the chain (amino terminus) therefore has a free amino group, while the terminal amino acid at the other end of the chain (carboxy terminus) has a free carboxyl group.

The term "amino terminus" (abbreviated N-terminus) refers to the free α-amino group on an amino acid at the amino terminal end of a peptide or to the α-amino group (imino group when participating in a peptide bond) of an amino acid at any other location within the peptide. Similarly, the term "carboxy terminus" refers to the free carboxyl group on the carboxy terminal end of a peptide or the carbonyl group of an amino acid at any other location within the peptide. Typically, amino acids comprising a polypeptide are numbered in order, increasing from the amino terminal to the carboxy terminal of the polypeptide. Thus when one amino acid is said to "follow" another, that amino acid is positioned closer to the carboxy terminal of the polypeptide then the "preceding" amino acid.

The term "domain" refers to a characteristic region of a polypeptide. The domain may be characterized by a particular structural feature such as a β turn, an α helix, or a β pleated sheet; by characteristic constituent amino acids (e.g. predominantly hydrophobic or hydrophilic amino acids, or repeating amino acid sequences); or by its location in a particular region of the folded three dimensional polypeptide. A domain may be composed of a series of contiguous amino acids or by amino acid sequences separated from each other in the chain, but brought into proximity by the folding of the polypeptide.

The term "subdomain" refers to a characteristic region within a domain. Subdomains also may be characterized by particular structural features, characteristic constituent amino acids or repeating amino acid sequences, or their localization in a particular region of the folded three dimensional polypeptide. For example, a polypeptide normally localized on the cell surface may possess a transmembrane domain characterized by hydrophobic amino acids. This domain may be composed of several distinct hydrophobic regions which, while not contiguous in the chain, lie alongside each other forming a hydrophobic domain when the molecule is folded. Each hydrophobic sequence may be characterized by a subdomain composed of repeats of particular non-polar amino acids e.g. leucine and valine.

The phrase "cysteine linkage" is a covalent linkage, either direct or through a series of covalently linked molecules that join two cysteine amino acids together in a peptide. The most common cysteine linkage is the disulfide bond characterized by a covalent linkage through two sulphur atoms. Where the linkage joins two cysteines in the same amino acid chain, the linkage is said to be an intra-chain linkage.

The term "peptide bridge" refers to an amino acid sequence that links together two other amino acid sequences. Although a peptide bridge may occur naturally, more commonly a peptide bridge is created artificially in order to link two distinct amino acid sequences. A peptide bridge may be used to join the biologically active regions of a polypeptide while eliminating the portions of the polypeptide that are not essential for a particular biological activity. The peptide bridge may be "designed" so as to maintain critical spatial (conformational) relationships between the active regions of the polypeptide.

The term "β turn" is defined by four residues designated as i, i+1, i+2, and i+3, which serve to reverse the direction of the polypeptide chain, with residues i and i+3 being hydrogen bonded to each other.

The phrase "a first cysteine" refers to the cysteine closest to the amino terminus of a native ligand that participates in the formation of an intra-chain disulfide bond. There are six cysteines in the native ligands for Class I RTKs that participate in the formation of intra-chain disulfide bonds. These cysteines are designated cysteine one through cysteine six or, alternatively a first cysteine through a sixth cysteine, proceeding from the amino- to the carboxy terminus of the polypeptide. Disulfide bonds join cysteines one and three, cysteines two and four, and cysteines five and six respectively. Thus, for example, in the native ligand, transforming growth factor alpha (TGF-α), "a first cysteine" refers to the cysteine in the 8th residue position from the amino terminus (designated Cys8). Similarly "a second cysteine", "a third cysteine", "a fourth cysteine", "a fifth cysteine", and "a sixth cysteine" correspond to "Cys16", "Cys21", "Cys32", "Cys34" and "Cys43", respectively. Disulfide bonds in this molecule exist between Cys8 and Cys21, Cys16 and Cys32, and Cys34 and Cys43, respectively. In the modified RTK ligands of the present invention, cysteine one is eliminated, leaving only two disulfide bridges. The cysteines, however, retain the same numbering as in the native ligand. Thus, the cysteines forming the disulfide bridge closest to the carboxy terminus of the modified ligand are still numbered five and six, respectively, even though there are only four cysteines participating in cysteine linkages.

The phrase "biologically active" refers to a peptide sequence that will interact with naturally occurring biological molecules to either activate or inhibit the function of those molecules in vitro or in vivo. The term is most commonly used herein to refer to regions of growth factor polypeptides which are responsible for the binding of the growth factor to the RTK, or for the activation or inhibition of RTKs.

The phrase "receptor tyrosine kinase(s)" or "RTK(s)" refer to polypeptides which are cell surface receptors with tyrosine kinase activity. When bound by a native ligand, they typically act to phosphorylate tyrosine residues of intracellular polypeptides.

The phrase "corresponds to" refers to the existence of structural features common to both the native and the modified ligand. Thus, the third disulfide bridge between cysteines five and six in domain C of the native RTK ligand corresponds to the disulfide bridge between cysteines five and six in domain $C_1$ of the modified RTK ligand. Correspondences between the native and the modified RTK ligands are most easily determined by reference to those cysteines that form intra-chain disulfide bridges (e.g. cysteines five and six, which are always present in both the native and modified ligands).

The phrase "therapeutically effective amount" refers to that amount of a modified RTK ligand which, when administered to a mammal in need thereof, is sufficient to effect treatment, defined as preventing or halting tumor growth. The amount of the modified RTK ligand which constitutes a "therapeutically effective amount" will vary depending on the ligand, the disease-state and its severity, and the mammal to be treated, but can be determined routinely by one of ordinary skill in the art having regard to his own knowledge and to this disclosure.

The terms "treating" or "treatment" refer to the treatment of a disease-state in a mammal, particularly in a human, which disease-state is alleviated by inhibition or activation of a particular RTK.

The phrase "pharmaceutically acceptable excipient" refers to an acceptable carrier, and any pharmaceutically acceptable auxiliary substance as required to approximate physiological conditions, which are non-toxic and do not effect the biological activity of the pharmaceutical composition suspended or included within it.

BRIEF DESCRIPTION OF THE DRAWINGS

FIG. 3 illustrates the results of a standard curve for a specific binding assay as described in Example 2.

FIGS. 4A and 4B show sequence data for a large number of Class I Receptor Tyrosine Kinase ligands. FIG. 4A contains information for EGF Receptor Ligands and FIG. 4B contains sequence data for additional HER ligands.

Structure of the Modified RTK Ligands

Figure 1:
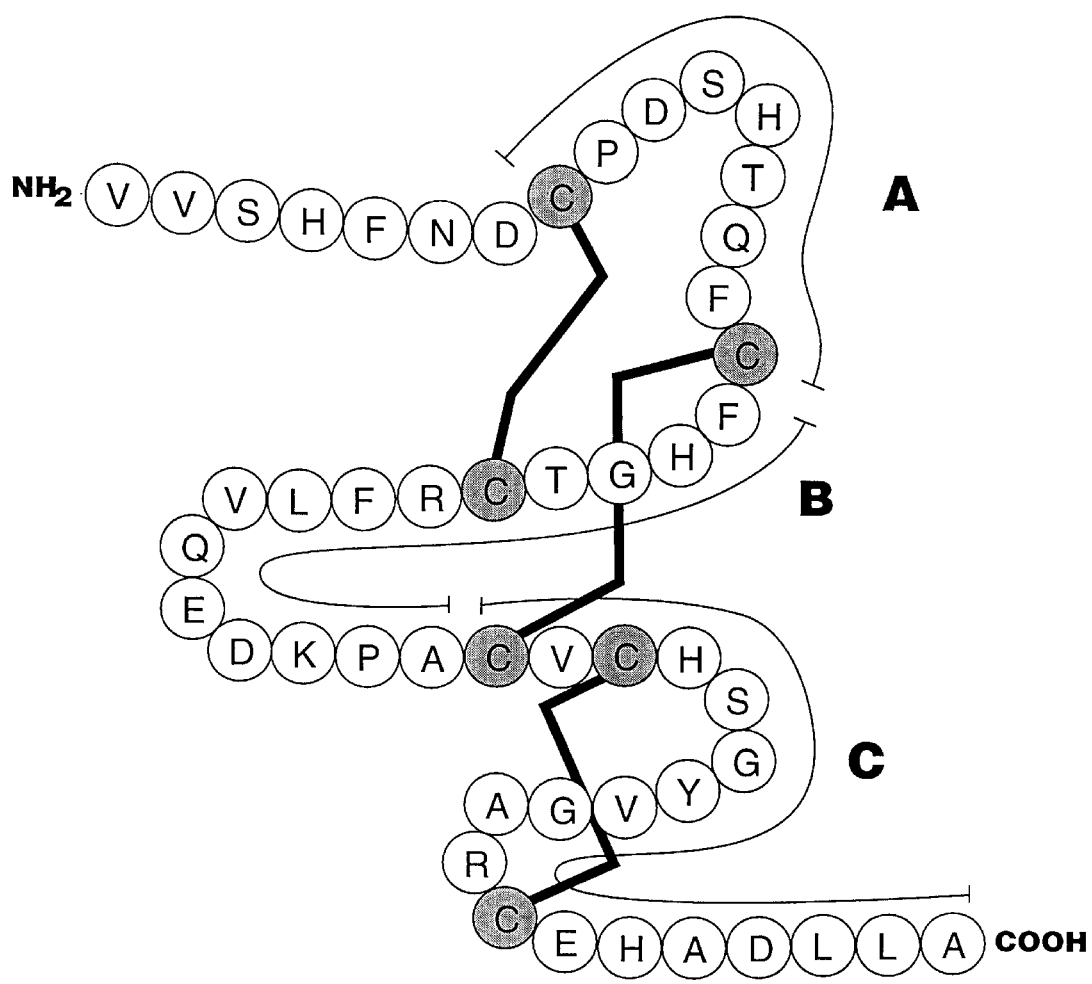
FIG. 1 illustrates the structure of transforming growth factor alpha (TGF-α), a native RTK ligand. TGF-α is characterized by the presence of six cysteine residues that form three disulfide bridges linking different regions of the same polypeptide. The disulfide bridges are formed between the first and third, the second and fourth, and the fifth and sixth cysteines, counting from the amino terminus. In addition TGF-α is characterized by three domains designated A, B, and C. Domain A consists of the first cysteine, those amino acids situated between the first and second cysteines, and the second cysteine. Domain C consists of cysteine four and those amino acids joined to the carboxy terminus of cysteine four. Domain B consists of those amino acids between the second and fourth cysteines and is characterized by the presence of a β turn.

The modified RTK ligands of the present invention correspond in structure to native RTK ligands and are therefore described herein by reference to the native RTK ligands, which are structurally a highly conserved group of polypeptides. Transforming growth factor alpha (TGF-α) is one such native RTK ligand. It is a polypeptide 50 amino acids in length. It contains six cysteines which form three intra-chain cysteine linkages (disulfide bridges). When the cysteine residues that participate in linkages are numbered in increasing order from the amino terminus of the polypeptide, the linkages are formed between cysteines one and three, cysteines two and four, and cysteines five and six. The three cysteine linkages effectively fold the molecule into three loops; an amino terminal A loop, a middle B loop, and a carboxy terminal C loop. These three loops correspond to three domains: Domain A, which consists of the first cysteine, those amino acids situated between the first and second cysteines, and the second cysteine; domain B, which consists of the amino acids situated between the second and fourth cysteines; and domain C, which consists of cysteine four and those amino acids attached to the carboxy terminus of cysteine four (see FIG. 1).

Figure 2:
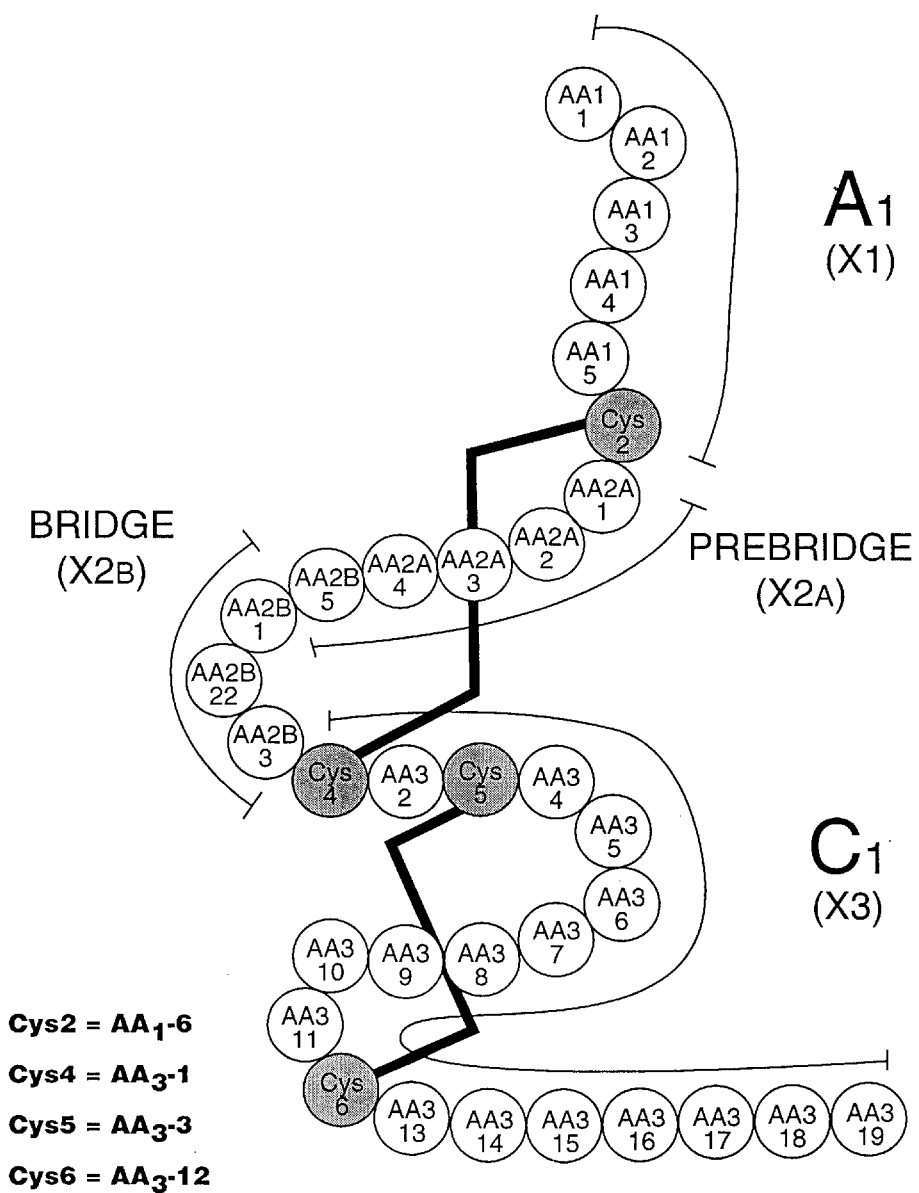
FIG. 2 illustrates the structure of a modified RTK ligand of the present invention. The $A_1$ domain of the modified RTK ligand corresponds to the A domain of the native RTK ligand. In the modified RTK ligand shown here, the first 10 amino acids, including cysteine one, of the $A_1$ domain are removed. Cysteine three is also removed and, in contrast to the native RTK ligand, there is no first cysteine linkage (disulfide bridge). Cysteines two and four are joined by a peptide bridge which includes a prebridge subdomain ($X2_A$) and a bridge subdomain ($X2_B$). Within the peptide bridge, a structure exists which corresponds to the β turn present in a native RTK ligand. Similarly, the $C_1$ domain corresponds to the C domain of the native RTK ligand and the two remaining cysteine linkages correspond to linkages two and three of the native RTK ligand.

The modified RTK ligands of the present invention eliminate domain B of the native RTK ligand and replace it with a peptide bridge that joins cysteine two with cysteine four. In describing these modified RTK ligands, domain $A_1$ of the modified RTK ligand corresponds to domain A of a native RTK ligand, and domain $C_1$ of the modified RTK ligand corresponds to domain C of a native RTK ligand. The peptide bridge consists of a prebridge subdomain and a bridge subdomain. Combination of residues from these two subdomains allows formation of a β turn which corresponds to the β turn in a native RTK ligand. The β turn is linked to the amino terminus of cysteine 4. The first cysteine linkage found in a native RTK ligand (between cysteines one and three) is therefore eliminated. In addition, the $A_1$ domain of the modified RTK ligand may be truncated by eliminating up to ten amino terminal amino acids present in the corresponding A domain of a native RTK ligand (see FIG. 2).

To summarize, the modified RTK ligands of this invention are analogous to the native RTK ligand described above in that:

1) They have four cysteine amino acids corresponding to cysteines two, four, five and six of the native RTK ligand;
2) They contain two cysteine linkages between cysteines two and four, and five and six, respectively;
3) They have domains $A_1$ and $C_1$ which have amino acid sequences that correspond essentially to the A and C regions, respectively, of the native RTK ligands; and
4) They both contain a β-turn.

Preferred Embodiments

The modified RTK ligands of the present invention consist essentially of the formula:

$$X1\text{-}X2_A\text{-}X2_B\text{-}X3$$

where each part of the formula corresponds to a domain of the modified RTK ligand described above in the Summary of the Invention. In particular, X1 (consisting of amino acid residues $AA_1$-1 through $AA_1$-6) corresponds to domain $A_1$; $X2_A$ is the prebridge subdomain (amino acid residues $AA_{2A}$-1 through $AA_{2A}$-5); $X2_B$ is the bridge subdomain (consisting of from one to three amino acid residues, $AA_{2B}$-1 through $AA_{2B}$-3); and X3 (amino acid residues $AA_3$-1 through $AA_3$-19) corresponds to domain $C_1$. Subdomains $X2_A$ and $X2_B$ together comprise the peptide bridge domain.

The preferred group of amino acid residues within this formula is as follows:

for X1, $AA_1$-1 is Ser, Lys, Asp, Gln, or Glu; $AA_1$-2 is His, Tyr, Phe, Gly, Gln, or Glu; $AA_1$-3 is Thr, Asp, Lys, Glu, Val, or Gln; $AA_1$-4 is Gln, Gly, Thr, Ala, His, Asp, or Asn; $AA_1$-5 is Phe or Tyr; and $AA_1$-6 is Cys;

for $X2_A$, $AA_{2A}$-1 is Val, Ile, Phe, His, Tyr, or Leu; $AA_{2A}$-2 is Asn, His, or Ile; $AA_{2A}$-3 is Gly, Asp, His, or Asn; $AA_{2A}$-4 is Gly, Asp, Thr, Glu, or Arg; and $AA_{2A}$-5 is Val, Thr, Glu, His, Gln, or a peptide bond;

for $X2_B$, when $X2_B$ consists of one amino acid residue, $AA_{2B}$-1 is Gly or Ser; or when $X2_B$ consists of two amino acid residues,
 1) $AA_{2B}$-1 is Asp, Ser, Thr, or Pro and $AA_{2B}$-2 is Asp, Ser, Asn, or Arg; or
 2) $AA_{2B}$-1 is Pro and $AA_{2B}$-2 is Gly or Asn; or
 3) $AA_{2B}$-1 is Gly, Asn or Asp and $AA_{2B}$-2 is Gly; or
 4) $AA_{2B}$-1 is Gly and $AA_{2B}$-2 is Ser, Glu, Thr, Asn, Ala, Gly, Asp, or Lys.

or, when $X2_B$ consists of three amino acid residues $AA_{2B}$-1 is any amino acid residue and:
 1) $AA_{2B}$-2 is Asp, Ser, Thr, or Pro and $AA_{2B}$-3 is Asp, Ser, Asn, or Arg; or
 2) $AA_{2B}$-2 is Pro and $AA_{2B}$-3 is Gly or Asn; or
 3) $AA_{2B}$-2 is Gly, Asn, or Asp and $AA_{2B}$-3 is Gly; or
 4) $AA_{2B}$-2 is Gly and $AA_{2B}$-3 is Ser, Glu, Thr, Asn, Ala, Gly, Asp, or Lys; and for $X_3$, $AA_3$-1 is Cys; $AA_3$-2 is Val, Asn, Lys, Arg, Ala, His, Thr, or Ile; $AA_3$-3 is Cys, $AA_3$-4 is His, Val, Pro, Ser, Arg, Glu, Ala, or Gln; $AA_3$-15 is Ser, Ile, Val, Thr, Pro, His, Asn, Lys, or Gln; $AA_3$-6 is Gly, Asn, Asp, Ser, Ala, Phe, or Glu; $AA_3$-7 is Tyr, Ser, or Phe; $AA_3$-8 is Val, Ile, Ser, Thr, Phe, Glu, Tyr, or His; $AA_3$-9 is Gly; $AA_3$-10 is Ala, Glu, Asn, Asp, Ile, Ser, Arg, or Val; $AA_3$-11 is Arg or Asn; $AA_3$-12 is Cys; $AA_3$-13 is Glu, Gly, Gln, Phe, Thr, or His; $AA_3$-14 is His, Tyr, Thr, Glu, Gly, Phe, Arg, Leu, or Asn; $AA_3$-15 is Ala, Arg, Gln, Leu, Lys, Val, Ile, Asn, Asp, or Tyr; $AA_3$-16 is Asp, Val, Asn, Thr, Gly, or Ser; $AA_3$-17 is Leu, Met, Arg, Asn, Val, or Pro; $AA_3$-18 is Leu, Lys, Asn, Arg, Asp, Met, Pro, Val, Ile, Phe, or Ala; and $AA_3$-19 is Ala, Trp, Val, Thr, Lys, Tyr, Asp, Glu, Phe, or Ser.

Within this preferred group, one preferred subgroup are modified RTK ligands directed toward the EGF receptor having the following formula:

for X1, $AA_1$-1 is Ser, Lys, Gln, Asp, or Glu; $AA_1$-2 is His, Tyr, Gly, or Phe; $AA_1$-3 is Thr, Asp, Lys, Glu, or Gln; $AA_1$-4 is Gln, Gly, Asn, His, or Asp; $AA_1$-5 is Phe or Tyr; and $AA_1$-6 is Cys;

for $X2_A$, $AA_{2A}$-1 is Phe, Ile, or Leu; $AA_{2A}$-2 is His, Ile, or Asn; $AA_{2A}$-3 is Gly, Asn, or Asp; $AA_{2A}$-4 is Thr, Glu, Asp, Arg, or Gly; and $AA_{2A}$-5 is Val, Thr or a peptide bond;

for X2$_B$, the amino acid residues are the same as in the preferred group; and for X3, AA$_3$-1 is Cys; AA$_3$-2 is Val, Lys, Ile, His, Arg, or Asn; AA$_3$-3 is Cys; AA$_3$-4 is His, Gln, Ser, Arg, Glu, or Val; AA$_3$-5 is Ser, Ile, Val, Pro, His, Lys, or Gln; AA$_3$-6 is Glu, Asn, Asp, or Gly; AA$_3$-7 is Tyr; AA$_3$-8 is Val, Ile, Ser, Phe, Glu, Thr, or His; AA$_3$-9 is Gly; AA$_3$-10 is Ala, Glu, Asp, Ser, Ile, or Val; AA$_3$-11 is Arg; AA$_3$-12 is Cys; AA$_3$-13 is Glu, Gln, His, or Gly; AA$_3$-14 is His, Tyr, Thr, Glu, Phe, Arg, or Gly; AA$_3$-15 is Ala, Arg, Gln, Leu, Val, Ile, or Lys; AA$_3$-16 is Asp, Thr, Val, Asn, or Ser; AA$_3$-17 is Leu or Met; AA$_3$-18 is Leu, Lys, Arg, Asp, Val, Ile, Phe, or Pro; and AA$_3$-19 is Ala, Trp, Val, Thr, Asp, or Tyr.

Within this subgroup, a preferred class are modified RTK ligands having the following formula:

for X1, AA$_1$-1 is Ser; AA$_1$-2 is His; AA$_1$-3 is Thr; AA$_1$-4 is Gln; AA$_1$-5 is Phe; and AA$_1$-6 is Cys;

for X$_{2A}$, AA$_{2A}$-1 is Phe; AA$_{2A}$-2 is His; AA$_{2A}$-3 is Gly; AA$_{2A}$-4 is Thr; and AA$_{2A}$-5 is a peptide bond;

for X$_{2B}$, the amino acids are the same as described above for the preferred group; and for X3, AA$_3$-1 is Cys; AA$_3$-2 is Val; AA$_3$-3 is Cys; AA$_3$-4 is His; AA$_3$-5 is Ser; AA$_3$-6 is Gly; AA$_3$-7 is Tyr; AA$_3$-8 is Val; AA$_3$-9 is Gly; AA$_3$-10 is Ala; AA$_3$-11 is Arg; AA$_3$-12 is Cys; AA$_3$-13 is Glu; AA$_3$-14 is His; AA$_3$-15 is Ala; AA$_3$-16 is Asp; AA$_3$-17 is Leu; AA$_3$-18 is Leu; and AA$_3$-19 is Ala.

Within this class, the most preferred modified RTK ligands of this invention are as follows:

1. Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1);
2. Ser-His-Thr-Gln-Phe-Cys-Phe-His-Gly-Thr-Ser-Cys-Val-Cys-His-Ser-Gly-Tyr-Val-Gly-Ala-Arg-Cys-Glu-His-Ala-Asp-Leu-Leu-Ala (SEQ ID NO: 2);
3. Ser-His-Thr-Gln-Phe-Cys-Phe-His-Gly-Thr-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 3);
4. Ser-His-Thr-Gln-Phe-Cys-Phe-His-Gly-Thr-Ser-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 4);
5. Ser-His-Thr-Gln-Phe-Cys-Phe-His-Gly-Thr-Ser-Pro-Asn-Cys-Val-Cys-His-Ser-Gly-Tyr-Val-Gly-Ala-Arg-Cys-Glu-His-Ala-Asp-Leu-Leu-Ala (SEQ ID NO: 5).

Within the preferred group of modified RTK ligands described above, another preferred subgroup are modified RTK ligands for other RTKs having the following formula:

for X1, AA$_1$-1 is Lys, AA$_1$-2 is Glu or Gln; AA$_1$-3 is Lys, Val, or Glu; AA$_1$-4 is Thr, Ala, Asn, or Gly; AA$_1$-5 is Phe or Tyr; and AAl-6 is Cys;

for X$_{2A}$, AA$_{2A}$-1 is Val, Leu, Tyr, or His; AA$_{2A}$-2 is Asn; AA$_{2A}$-3 is His or Gly; AA$_{2A}$-4 is Gly; AA$_{2A}$-5 is His, Gln, Thr, or Glu;

for X$_{2B}$, the amino acids are the same as described above for the preferred group; and for X3, AA$_3$-1 is Cys; AA$_3$-2 is Arg, Thr, Ala, or Lys; AA$_3$-3 is Cys; AA$_3$-4 is Pro, Ala, or Gln; AA$_3$-5 is Asn, Thr, or Pro; AA$_3$-6 is Gly, Glu, Ala, Ser, or Phe; AA$_3$-7 is Phe or Ser; AA$_3$-8 is Ile, Tyr, or Thr; AA$_3$-9 is Gly; AA$_3$-10 is Ala, Asn, Arg, Glu, or Asp; AA$_3$-11 is Asn or Arg; AA$_3$-12 is Cys; AA$_3$-13 is Glu, Phe, Gln or Thr; AA$_3$-14 is Glu, Leu, His, or Asn; AA$_3$-15 is Asn, Ala, Leu, Asp, or Tyr; AA$_3$-16 is Gly, Ser, or Val; AA$_3$-17 is Met, Asn, Val, Arg, or Pro; AA$_3$-18 is Met, Asn, Lys, or Ala; and AA$_3$-19 is Lys, Phe, Glu, or Ser.

Within this subgroup, a preferred class are modified RTK ligands having the following formula:

for X1, AA$_1$-1 is Lys; AA$_1$-2 is Glu; AA$_1$-3 is Lys; AA$_1$-4 is Thr; AA$_1$-5 is Phe; AA 1-6 is Cys;

for X$_{2A}$, AA$_{2A}$-1 is Val; AA$_{2A}$-2 is Asn; AA$_{2A}$-3 is Gly; AA$_{2A}$-4 is Gly; AA$_{2A}$-5 is Glu;

for X$_{2B}$, the amino acids are the same as described above for the preferred group; and for X3, AA$_3$-1 is Cys; AA$_3$-2 is Lys; AA$_3$-3 is Cys; AA$_3$-4 is Gln; AA$_3$-5 is Pro; AA$_3$-6 Gly; AA$_3$-7 is Phe; AA$_3$-8 is Thr; AA$_3$-9 is Gly; AA$_3$-10 is Ala; AA$_3$-11 is Arg; AA$_3$-12 is Cys; AA$_3$-13 is Thr; AA$_3$-14 is Glu; AA$_3$-15 is Asn; AA$_3$-16 is Val; AA$_3$-17 is Pro; AA$_3$-18 is Met; and AA$_3$-19 is Lys.

Within this class, the most preferred modified RTK ligands of this invention are as follows:

1. Lys-Glu-Lys-Thr-Phe-Cys-Val-Asn-Gly-Gly-Glu-Gly-Cys-Lys-Cys-Gln-Pro-Gly-Phe-Thr-Gly-Ala-Arg-Cys-Thr-Glu-Asn-Val-Pro-Met-Lys (SEQ ID NO: 6);
2. Lys-Glu-Lys-Thr-Phe-Cys-Val-Asn-Gly-Gly-Glu-Ser-Cys-Lys-Cys-Gln-Pro-Gly-Phe-Thr-Gly-Ala-Arg-Cys-Thr-Glu-Asn-Val-Pro-Met-Lys (SEQ ID NO: 7);
3. Lys-Glu-Lys-Thr-Phe-Cys-Val-Asn-Gly-Gly-Glu-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 8);
4. Lys-Glu-Lys-Thr-Phe-Cys-Val-Asn-Gly-Gly-Glu-Ser-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 9);
5. Lys-Glu-Lys-Thr-Phe-Cys-Val-Asn-Gly-Gly-Glu-Ser-Pro-Asn-Cys-Lys-Cys-Gln-Pro-Gly-Phe-Thr-Gly-Ala-Arg-Cys-Thr-Glu-Asn-Val-Pro-Met-Lys (SEQ ID NO: 10).

Preparation of Modified RTK Ligands

A. Chemical Synthesis of Modified Ligands

The modified RTK ligands of this invention are typically no more than 100 amino acids in length. It is therefore feasible to prepare the ligands using any of a number of chemical peptide synthesis techniques well known to those of skill in the art including both solution methods and solid phase methods, with solid phase synthesis being preferred.

Solid phase synthesis in which the C-terminal amino acid of the sequence is attached to an insoluble support followed by sequential addition of the remaining amino acids in the sequence is the preferred method for preparing the modified RTK ligands of the present invention. Techniques for solid phase synthesis are described by Barany and Merrifield, *Solid-Phase Peptide Synthesis*, pp. 3–284 in *The Peptides: Analysis, Synthesis, Biology*. Vol. 2: *Special Methods in Peptide Synthesis*, Part A., Merrifield, et al. *J. Am. Chem. Soc.* 85, 2149–2156 (1963), and Gross and Meienhofer, eds. Academic Press, New York, 1980 and Stewart et al., *Solid Phase Peptide Synthesis*, 2nd ed. Pierce Chem. Co., Rockford, Ill. (1984) which are incorporated herein by reference.

Solid phase synthesis is started from the C-terminal end of the peptide by coupling a protected amino acid via its carboxyl group to a suitable solid support. The solid support is not particularly limited as long as it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Solid support materials are well known to those of skill in the art and include, but are not limited to halomethyl resins, such as chloromethyl resin or bromomethyl resin; hydroxymethyl resins, phenol resins, tert-alkyloxycarbonylhydrazidated resins and the like. The resins are commercially available and their preparation is known by one of ordinary skill in the art.

The acid form of peptides may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the polypeptide from the solid support produces a polypeptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, and hydroxyl) which must also be protected with appropriate protecting groups to prevent chemical reactions from occurring at those sites during the polypeptide synthesis. Protecting groups are well known to those of skill in the art. See, for example, Gross and Meienhofer, *The Peptides: Analysis, Synthesis, Biology*, Vol. 3: *Protection of Functional Groups in Peptide Synthesis*, Academic Press, New York. (1981) which is incorporated herein by reference.

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Side-chain protecting groups must be chosen to render the side chain functional group inert during the synthesis, must be stable under the conditions used to remove the α-amino protecting group, and must be removable after completion of the polypeptide synthesis under conditions that will not alter the structure of the polypeptide.

Illustrative examples of protecting groups for an α-amino group include aromatic urethane-type groups, such as fluorenylmethyloxycarbonyl (Fmoc), Cbz, and substituted benzyloxycarbonyl, such as, for example, p-chlorobenzyloxycarbonyl, o-chlorobenzyloxycarbonyl, 2,4-dichlorobenzyloxycarbonyl, 2,6-dichlorobenzyloxycarbonyl, and the like; aliphatic urethane-type groups such as Boc, t-amyloxycarbonyl, isopropyloxycarbonyl, 2-(p-biphenyl)isopropyloxycarbonyl, allyloxycarbonyl, and the like, cycloalkyl urethane-type groups such as cyclopentyloxycarbonyl, cyclohexyloxycarbonyl, cycloheptyloxycarbonyl, adamantyloxycarbonyl, and the like. The preferred α-amino protecting groups is t-butyloxycarbonyl (Boc).

For the side chain amino group present in Lys, any of the protecting groups described above for the protection of the α-amino group are suitable. Typical groups include, but are not limited to, Boc, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred side chain amino protecting group is o-chlorobenzyloxycarbonyl (2-ClZ).

For protection of the guanidino group of Arg, examples of suitable protecting groups include, but are not limited to, nitro, tosyl, Cbz, adamantyloxycarbonyl, and Boc. The preferred protecting group is tosyl (Tos).

The hydroxyl group on the side chains of Ser, Thr, or Tyr may be protected by a $C_1$–$C_4$ alkyl, such as methyl, ethyl, and t-butyl; substituted benzyl such as p-methoxybenzyl, p-nitrobenzyl, p-chlorobenzyl, o-chlorobenzyl, and 2,6-dichlorobenzyl. The preferred aliphatic hydroxyl protecting group for Ser and Thr is benzyl, while the Tyr aromatic hydroxyl is most commonly protected as the 2,6-dichlorobenzyl ether.

The carboxyl group of Asp or Glu may be protected, for example, by esterification using groups such as benzyl, t-butyl, cyclohexyl, cyclopentyl, and the like. Preferred groups are benzyl and cyclohexyl.

Coupling of the amino acids may be accomplished by a variety of chemistries known to those of skill in the art. Typical approaches involve either the conversion of the amino acid to a derivative that will render the carboxyl group more susceptible to reaction with the free N-terminal amino group of the polypeptide fragment, or use of a suitable coupling agent such as N,N'-dicyclohexylcarbodiimide (DCC) or N,N'-diisopropylcarbodiimide (DIPCDI). Appropriate synthesis chemistries are disclosed in Gross and Meienhofer, *The Peptides: Analysis, Structure, Biology*, Vol. 1: *Methods of Peptide Bond Formation*, Academic Press, New York. (1979) and Izumiya, et al., *Synthesis of Peptides*, Maruzen Pub. Co., Ltd., (1975), both of which are herein incorporated by reference.

Polypeptide synthesis is commenced by first coupling the C-terminal amino acid which is protected at the Nα-amino position by a protecting group such as t-butyloxycarbonyl to a solid support. For example, Boc-Gly-OH can be coupled to the benzhydrylamine resin using isopropylcarbodiimide at about 25° C. for two hours with stirring. Following the coupling of the Boc protected amino acid to the resin support, the α-amino protecting group is removed, using trifluoroacetic acid (TFA) in methylene chloride or TFA alone. This deprotection is carried out at a temperature between about 0° C. and room temperature.

After removal of the α-amino protecting group, the remaining Boc-protected amino acids are coupled stepwise in the desired order. Appropriately protected amino acids are commercially available from a number of suppliers (e.g. Applied Biosystems, Foster City, Calif.). As an alternative to the stepwise addition of individual amino acids, appropriately protected peptide fragments consisting of more than one amino acid may also be coupled to the "growing" polypeptide. Selection of an appropriate coupling reagent, as explained above, is well known to those of skill in the art.

Each protected amino acid or amino acid sequence is introduced into the solid phase reactor in excess and the coupling is carried out in a medium of dimethylformamide (DMF) or methylene chloride ($CH_2Cl_2$) or mixtures thereof. If coupling is incomplete, the coupling reaction may be repeated before deprotection of the Nα-amino group and addition of the next amino acid. Coupling efficiency may be monitored by a number of means well known to those of skill in the art. A preferred method of monitoring coupling efficiency is by the ninhydrin reaction. Polypeptide synthesis reactions may be performed automatically using a number of commercially available peptide synthesizers (e.g. Biosearch 9500, Biosearch, San Raphael, Calif.).

The peptide can be cleaved and the protecting groups removed by either stirring the insoluble carrier or solid support in anhydrous, liquid hydrogen fluoride (HF) in the presence of anisole and dimethylsulfide at about 0° C. for about 20 to 90 minutes, preferably 60 minutes or by bubbling hydrogen bromide (HBr) continuously through a 1 mg/10 ml suspension of the resin in trifluoroacetic acid (TFA) for 30 to 60 minutes at about room temperature, depending on the protecting groups selected. Other deprotection methods well known to those of skill in the art may also be used.

Following deprotection and cleavage, the free amino terminus can be acetylated with an acetylating agent, such as acetic anhydride.

The modified ligands of the present invention can be isolated and purified from the reaction mixture by means of peptide purification well known to those of skill in the art. For example, the polypeptides may be purified using gel electrophoresis or known chromatographic procedures such as reverse phase HPLC, gel permeation, ion exchange, size exclusion, affinity, partition, or countercurrent distribution.

B. Biological Synthesis of Modified Ligands

1. Isolation of DNA Sequences Encoding Modified Ligands

The modified RTK ligands of the present invention may also be prepared using methods of recombinant DNA technology. Generally this involves synthesizing or isolating a DNA sequence that encodes the particular RTK ligand, placing the DNA sequence into a plasmid or other vector such that it is under the control of a transcription promoter, inserting the vector into an appropriate organism, such as bacterial cells, yeast cells, or mammalian cells, to obtain expression of the desired polypeptide, and then isolating the polypeptide from the host cells.

The DNA sequence encoding a particular modified RTK ligand may be produced either de novo by synthesizing oligonucleotides which may be assembled together to produce the desired sequence, or alternatively by the modification of pre-existing native DNA sequences.

Where the DNA is synthesized de novo, the constituent oligonucleotides can be chemically synthesized by a variety of methods known to those of skill in the art. These include the solid phase phosphoramidite method described by Beaucage and Carruthers, *Tetra. Letts.* 22: 1859–1862 (1981), the triester method according to Matteucci, et al., *J. Am. Chem. Soc.*, 103:3185 (1981), both incorporated herein by reference, or by other methods known to those of skill in the art. It is preferred that the DNA be synthesized using standard β-cyanoethyl phosphoramidites on a commercially available DNA synthesizer (e.g. from Applied Biosystems, Foster City, Calif.) using standard protocols.

The oligonucleotides may be purified, if necessary, by techniques well known to those of skill in the art. Typical purification methods include, but are not limited to, size exclusion chromatography, gel electrophoresis, anion exchange chromatography (e.g. Mono-Q column, Pharmacia-LKB, Piscataway, N.J.), or reverse phase high performance liquid chromatography (HPLC).

The oligonucleotides are then annealed to their complements to produce double-stranded DNA sequences. Alternatively, the double stranded sequence can be formed by DNA polymerase using the single strand as a template with an appropriate primer. Where the complementary oligonucleotides are chemically synthesized, the oligonucleotides can be designed to provide overhangs when the oligonucleotides are annealed. The double stranded DNA sequences may then be annealed together via the overhangs to produce longer double-stranded DNA molecules, and the nicks at the overhangs can be ligated together using a ligase.

Methods of DNA hybridization and ligation are well known to those of skill in the art. See, for example, Sambrook et al., *Molecular Cloning—A Laboratory Manual*, Cold Spring Harbor Laboratory, Cold Spring Harbor, N.Y. (1985) which is incorporated herein by reference.

Alternatively, the DNA sequences encoding the modified RTK ligands can be obtained by altering pre-existing DNA sequences that encode native RTK ligands. The DNA sequences encoding a number of native ligands are known. A number of DNA constructs containing sequences encoding RTK ligands are available (See, for example, Holmes, W. E. et al., *Science* 256, 1205–1210 (1992); Derynk, R. et al., *Cell* 38, 287–297 (1984)) or alternatively, the DNA is isolated from a genomic or cDNA library using labelled oligonucleotide probes specific for sequences in the DNA. Restriction endonuclease digestion of genomic DNA or cDNA containing the gene encoding native RTK ligands can be used to isolate the DNA encoding these polypeptides. After restriction endonuclease digestion, DNA encoding RTK ligands is identified by its ability to hybridize with nucleic acid probes, for example on Southern blots, and these DNA regions are isolated by standard methods familiar to those of skill in the art. See Sambrook, et al.

DNA which normally encodes native RTK ligands must be modified to produce the modified RTK ligands of the present invention. The native DNA sequence may be modified by a variety of methods such as site-directed mutagenesis. These methods are well known to those of skill in the art. See for example, Botstein and Shortle, *Science*, 229: 1193–1201 (1985); Zoller and Smith, pages 468 to 500 in *Methods in Enzymology*, Vol. 100: *Mutagenesis*, Academic Press, Inc. New York. (1983); Gillman and Smith, *Gene*, 8:81–97 (1979) and Roberts et al., *Nature* 328: 731–734 (1987) which are incorporated herein by reference. The modifications are designed to alter the polypeptide sequence at the primary structure level by amino acid insertions, substitutions, deletions, and the like. These modifications can be used in a number of combinations to produce the DNA encoding the final modified polypeptide.

The polymerase chain reaction can also be used to prepare DNA encoding RTK ligands. Polymerase chain reaction technology (PCR) is used to amplify nucleic acid sequences encoding the RTK ligand directly from mRNA, from cDNA, and from genomic libraries or cDNA libraries. The isolated sequences encoding RTK ligands may be used as templates for PCR amplification.

Appropriate primers and probes for amplifying the RTK ligands are generated from analysis of the DNA sequences. In brief, oligonucleotide primers complementary to the two 3' borders of the DNA region to be amplified are synthesized. The polymerase chain reaction is then carried out using the two primers (see *PCR Protocols: A Guide to Methods and Applications*, Innis, et al., eds., Academic Press, San Diego (1990)). Primers can be selected to amplify the entire regions encoding EI-27 or to amplify smaller DNA segments as desired. Oligonucleotides for use as probes are chemically synthesized as described above.

2. Expression of Modified Ligands

Once the DNA encoding the modified RTK ligand is isolated and cloned, one may express the ligand in a recombinantly engineered cell such as bacteria, yeast, insect (especially employing baculoviral vectors), and mammalian cells. It is expected that those of skill in the art are knowledgeable in the numerous expression systems available for expression of the DNA encoding RTK ligands. No attempt to describe in detail the various methods known for the expression of proteins in prokaryotes or eukaryotes will be made.

In brief summary, the expression of natural or synthetic nucleic acids encoding RTK ligands will typically be achieved by operably linking the DNA or cDNA to a promoter (which is either constitutive or inducible), and then incorporating the promoter-DNA construct into an expression vector. The vector should be suitable for replication and integration in either prokaryotes or eukaryotes. Typical expression vectors contain transcription and translation terminators, initiation sequences, and promoters useful for regulation of the expression of the polynucleotide sequence encoding RTK ligand polypeptides. To obtain high level expression of a cloned gene, such as those polynucleotide sequences encoding RTK ligands, it is desirable to construct expression plasmids which contain, at the minimum, a strong promoter to direct transcription, a ribosome binding site for translational initiation, and a transcription/translation terminator.

a. Expression in Prokaryotes. Methods for the expression of cloned genes in bacteria are well known. See, for example, Maniatis et al. *Molecular Cloning, A Laboratory Manual*, Cold Spring Harbor Laboratory, Cold Spring Harbor, N.Y. (1982) which is incorporated herein by reference. Generally, to obtain high level expression of a cloned gene in a prokaryotic system, it is essential to construct expression vectors which contain, at the minimum, a strong promoter and regulator to direct mRNA transcription and termination. Examples of regulatory regions suitable for this purpose are the promoter and operator region of the *E. coli* β-galactosidase gene, the *E. coli* tryptophan biosynthetic pathway, or the leftward promoter from the phage lambda. The inclusion of selection markers in DNA vectors transformed in *E. coli* aid in the isolation of transformed bacteria. Examples of such markers include the genes specifying resistance to ampicillin, tetracycline, or chloramphenicol. In a preferred embodiment, pUC19 may be used as a vector for the subcloning and amplification of the desired gene sequences.

The RTK ligands produced by prokaryotic cells may not fold properly. During purification from *E. coli*, the expressed polypeptides may first be denatured and then renatured. This can be accomplished by solubilizing the bacterially produced proteins in a chaotropic agent such as guanidine HCl and reducing all cysteine residues with a reducing agent such as beta-mercaptoethanol. The polypeptides are then renatured, either by slow dialysis or by gel filtration (see U.S. Pat. No. 4,511,503).

b. Expression in Eukaryotes. A variety of eukaryotic expression systems such as yeast, insect cell lines and mammalian cells, are known to those of skill in the art. As explained briefly below, modified RTK ligands may also be expressed in these eukaryotic systems.

c. Expression in Yeast. Synthesis of heterologous proteins in yeast is well known and described. *Methods in Yeast Genetics*, Sherman, F., et al., Cold Spring Harbor Laboratory, (1982) is a well recognized work describing the various methods available to produce the RTK ligand polypeptides in yeast.

Examples of promoters for use in yeast include GAL1,10 (Johnson and Davies, *Mol. Cell. Biol.*, 4: 1440–1448 (1984)) ADH2 (Russell et al., *J. Biol. Chem.*, 258: 2674–2682 (1983)), PHO5 (*E.M.B.O.J.*, 6: 675–680, (1982)), and MFα1 (Herskowitz and Oshima, pp. 181–209 in *The Molecular Biology of the Yeast Saccharomyces*, Strathern et al., eds. Cold Spring Harbor Lab., Cold Spring Harbor, N.Y. (1982)). A multicopy plasmid with a selective marker such as Leu-2, URA-3, Trp-1, and His-3 is also desirable.

A number of yeast expression plasmids like YEp6, YEp13, YEp4 can be used as vectors. A gene of interest can be fused to any of the promoters in various yeast vectors. The above-mentioned plasmids have been fully described in the literature. See, for example, Botstein, et al., *Gene*, 8:17–24 (1979) and Broach et al., *Gene*, 8: 121–133 (1979).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs *Nature*, 275: 104–109 (1978) and Hinnen, et al. *Proc. Natl. Acad. Sci. USA*, 75: 1929–1933 (1978). The second procedure does not involve removal of the cell wall. Instead the cells are treated with lithium chloride or acetate and PEG and put on selective plates. Ito et al., *J. Bact.*, 153:163–168 (1983).

The RTK ligands can be isolated from yeast by lysing the cells and applying standard protein isolation techniques to the lysates. The monitoring of the purification process can be accomplished by using Western blot techniques or radioimmunoassays or other standard immunoassay techniques.

d. Expression in Mammalian and Insect Cell Cultures. The DNA sequences encoding modified RTK ligands can be ligated to various expression vectors for use in transforming host cell cultures. The vectors preferably contain a marker such as dihydrofolate reductase or metallothionein to provide a phenotypic trait for selection of transformed host cells. Cell cultures useful for the production of the RTK ligands are cells of insect or mammalian origin. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, Cos-7 or MDCK cell lines.

As indicated above, the vector, e.g., a plasmid, which is used to transform the host cell, preferably contains DNA sequences to initiate transcription and sequences to control the translation of the DNA sequence encoding the modified ligand. These sequences are referred to as expression control sequences. When the host cell is of insect or mammalian origin illustrative expression control sequences are obtained from the SV-40 promoter (*Science*, 222: 524–527 (1983)), the CMV I.E. promoter (*Proc. Natl. Acad. Sci.*, 81: 659–663 (1984)) or the metallothionein promoter (*Nature*, 296: 39–42 (1982)). The cloning vector containing the expression control sequences is cleaved using restriction enzymes and adjusted in size as necessary or desirable and ligated with polynucleotides coding for the RTK ligands by means well known in the art.

As with yeast, when higher animal host cells are employed, polyadenylation or transcription terminator sequences from known mammalian genes need to be incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague et al., *J. Virol.*, 45: 773–781 (1983)).

Additionally, gene sequences to control replication in the host cell may be incorporated into the vector such as those found in bovine papilloma virus type-vectors. See, for example, Saveria-Campo, at pp. 2133–238 in *DNA Cloning Vol. II A Practical Approach*, D. M. Glover, ed. IRL Press, Arlington, Va. (1985).

The host cells are competent or rendered competent for transformation by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation and microinjection of the DNA directly into the cells.

The transformed cells are cultured by means well known in the art. See, for example, Kuchler et al., *Biochemical Methods in Cell Culture and Virology*, (1977). The expressed RTK ligands are isolated from cells grown as suspensions or as monolayers. They are recovered by well known mechanical, chemical or enzymatic means.

e. Expression in recombinant vaccinia virus- or adenovirus-infected cells. In addition to use in recombinant expression systems, the DNA encoding RTK ligands can also be used to transform viruses that transfect host cells in vitro or in vivo. These transfected host cells, in turn express the modified ligand (see section on expression of modified RTK ligands in eukaryotic cells, above).

Suitable viruses for use in the present invention include, but are not limited to, pox viruses, such as canarypox and cowpox viruses, and vaccinia viruses, alpha viruses, adenoviruses, and other animal viruses. The recombinant viruses can be produced by methods well known in the art, for example, using homologous recombination or ligating two plasmids. A recombinant canarypox or cowpox virus can be made, for example, by inserting the polynucleotides encoding the RTK ligand polypeptides into plasmids so that they are flanked by viral sequences on both sides. The polynucleotides encoding the RTK ligand binding domains are then inserted into the virus genome through homologous recombination.

For example, a recombinant adenovirus can be produced by ligating together two plasmids each containing about 50% of the viral sequence and a nucleotide sequence encoding an RTK ligand polypeptide. Recombinant RNA viruses such as the alpha virus can be made via a cDNA intermediate using methods known in the art.

In the case of vaccinia virus (for example, strain WR), the nucleotide sequence encoding the RTK ligand can be inserted in the genome by a number of methods including homologous recombination using a transfer vector, pTKgpt-OFIS as described in Kaslow et al., *Science* 252:1310–1313 (1991), which is incorporated herein by reference.

Alternately the DNA encoding RTK ligands may be inserted into another plasmid designed for producing recombinant vaccinia, such as pGS62 (Langford et al., *Mol. Cell. Biol.* 6:3191–3199 (1986)). This plasmid consists of a cloning site for insertion of foreign genes, the P7.5 promoter of vaccinia to direct synthesis of the inserted gene, and the vaccinia TK gene flanking both ends of the foreign gene.

Confirmation of production of recombinant virus can be achieved by DNA hybridization using cDNA encoding RTK ligands and by immunodetection techniques using antibodies specific for the expressed RTK ligands. Virus stocks may be prepared by infecting cells and harvesting virus progeny.

3. Purification of Modified Ligands

The modified RTK ligands produced by recombinant DNA technology may be purified by standard techniques well known to those of skill in the art. Where the recombinant protein is secreted directly into the media the media is collected directly. Where the protein is retained either in solution within the cell or as an inclusion body, the cell must be lysed to recover the protein. This is typically accomplished by sonification or maceration.

In either case, the protein is then typically isolated from the cellular debris by filtration, centrifugation, or other means known to those of skill in the art, usually by filtration or centrifugation. The protein is then concentrated by adsorption to any suitable resin such as, for example, Q Sepharose or metal chelators, by ammonium sulfate fractionation, polyethylene glycol precipitation, dialysis, or by ultrafiltration. Other means known in the art may be equally suitable.

If the modified RTK ligand is expressed as a fusion protein, it may be necessary to digest the fusion protein with an appropriate proteolytic enzyme or use chemical cleavage (i.e. cyanogen bromide) to release the desired modified RTK ligand.

Purification of the modified RTK ligands may require the additional use of, for example, gel electrophoresis, capillary electrophoresis, reverse phase HPLC, affinity chromatography, ion exchange chromatography, sizing chromatography or other protein purification techniques well known to those of skill in the art. See, for instance, Scopes, *Protein Purification: Principles and Practice*, Springer-Verlag: New York (1982), *Methods in Enzymology, Vol. 182: Guide to Protein Purification*. Deutscher, ed. Academic Press, Inc. N.Y. (1990) both of which are incorporated herein by reference.

Determination of Biological Activity of Modified RTK Ligands

In order for a modified RTK ligand to exhibit agonistic activity, it must both bind to an RTK and activate that receptor. Conversely, a modified RTK ligand may show antagonist activity by binding to and not activating the receptor. Thus in order to evaluate the agonistic or antagonistic activity of a modified RTK ligand it is desirable to assay both for binding affinity and for ability to activate the bound receptor.

A. Assaying Binding Affinity

Means of assaying for the binding affinity of a particular ligand for a cell-surface protein are well known to those of skill in the art. In typical binding assays, the putative ligand is immobilized and exposed to a labelled receptor or alternatively, an immobilized receptor is exposed to a labelled ligand. The immobilized moiety is then washed to remove any unbound material and the label is detected. The amount of immobilized label is proportional to the degree of binding between the receptor and the putative ligand.

In a preferred embodiment, cell membranes bearing the RTK are isolated and bound to a solid support (e.g. a polyvinylchloride plate, Dynatch, Arlington, Va.). The modified RTK ligand, labelled either radioactively (e.g. with $^{125}$I) or fluorescently (e.g. with fluorescein or rhodamine), is exposed to the bound receptor-bearing membranes. After washing, the membranes are isolated and the amount of bound modified RTK ligand is determined by measuring the radioactivity in a scintillation counter.

Binding is either determined directly or in competition with another RTK ligand. In a direct determination, the modified RTK ligand is labelled, and the amount of bound modified RTK ligand is directly measured. When the assay is performed as a competitive inhibition, a native RTK ligand is labelled. The membranes bearing the RTK are then exposed to the labelled ligand in the presence of varying amounts of the unlabelled modified RTK ligand. Where the modified RTK ligand has a high affinity for the RTK it will out-compete the native RTK ligand, resulting in a reduction of binding by the native RTK ligand. A detailed protocol illustrating the competitive binding assay is provided in Example 2.

B. Assaying Receptor Activation

Native RTK ligands are potent mitogens in a number of cells. For example, the EGF receptor is detectable on a large variety of cell types and responds to EGF by the enhancement of cell proliferation (Carpenter, *Ann. Rev. Biochem.*, 56: 881–914 (1987)). Thus, agonistic activity of RTK ligands may be determined simply by measuring the ability of the ligand to activate cells bearing appropriate receptors. Means of measuring activation are well known to those of skill in the art.

In a preferred embodiment, activation will be measured by determining the rate of tritiated thymidine uptake by the exposed cells. Metabolically active cells will incorporate a greater amount of thymidine and thus present a stronger signal. A protocol for assaying receptor activation by measuring uptake of tritiated thymidine is presented in Example 3 below.

Alternatively, the mitogenic activity of the modified ligands may be assayed by measuring the effect of the ligand on the growth rate of a particular target cell. Methods of conducting cell growth studies are well known to those of skill in the art (see, e.g., Cohen and Carpenter, *Proc. Natl. Acad. Sci. (U.S.A.)*, 72: 1317–1321 (1975)). Briefly, an assay of this sort merely requires establishing a culture of a cell line bearing the appropriate RTK. The cells are cultured for an appropriate period of time either in the presence or absence of the putative RTK ligand. Cell counts are take periodically by any of a number of means well known to those of skill in the art (e.g. subsampling and manual counting or automated counting via a coulter counter). Relative mitogenic activity may be determined by a comparison of the rate of cell proliferation or the final cell count in cultures containing the ligand with cell cultures without the ligand. An example of a cell proliferation study is presented in Example 2 below.

Agonist activity of the modified RTK ligand may also be assayed by exploiting other known biological activities of RTK ligands. For example, EGF is known to induce precocious eyelid opening in newborn mice and hypertrophy and hyperplasia of corneal epithelial cells in organ cultures. Modified ligand specific to EGF receptors with agonistic properties will also be expected to show similar activities. Thus eyelid opening activity may be assayed by subcutaneous injection of the modified ligand into a newborn mouse as described by Cohen, *J. Biol. Chem.*, 237: 1555–1562 (1973) and Cohen and Carpenter, *Proc. Nat. Acad. Sci. (U.S.A.)*, 72: 1317–1321 (1975). Induction of hypertrophy and hyperplasia may be assayed with organ cultures of chick embryo cornea using the method described by Savage and Cohen, *Exp. Eye Res.*, 15: 361–366 (1973). One of skill would recognize that these examples are only illustrative. Agonistic activity of a modified RTK ligand may measured by assaying for any known biological property of the corresponding native RTK ligand.

Use of Modified RTK Ligands as an Assay for Receptor Multiplication

The amplification of RTKs has been associated with the etiology of a number of cancers. In particular, the amplification of HER2/neu (sometimes called c-erbB2) has been correlated with the etiology of breast cancers. Indeed, the HER2/neu amplification is more predictive for clinical outcome than all other known prognosticators with the exception of positive lymph nodes (Slamon et al. *Science*, 244: 707–712 (1989)). Thus an assay for the presence or absence of c-erbB2 receptors provides a clinically useful diagnostic tool. Traditionally, these receptors have been assayed using solid blotting techniques (e.g. Southern, Western or Northern). Southern and Northern blotting, however, only assess over-expression at the DNA and RNA levels, respectively. Western blotting, while measuring protein expression, picks up intracellular as well as surface bound proteins. Thus these techniques do not provide a direct assay for amplification of membrane bound intact RTKs. Moreover, because of the presence of non-malignant cells in human tumor tissue, these techniques cannot determine whether an observed alteration or amplification is specific only for the malignant cells in the tissue, or common to all cells. Id. at 708.

The use of labelled ligands specific to HER2/neu (erb) receptors permits the detection of amplification of these receptors. One simply contacts the cells with the labelled modified RTK ligand and then visualizes the amount of specific binding in situ in either a cellular smear or in a histological section. Alternatively, membranes bearing receptors may be isolated from the cells in question and the receptor concentration may quantified by measuring the binding of a labelled ligand specific for those receptors. See Example 4 below.

Labels suitable for tagging polypeptide ligands are well known to those of skill in the art. A composition detectable by spectroscopic, photochemical, biochemical, immunochemical, or chemical means may provide a suitable label. For example, useful labels include $^{32}P$, $^{125}I$, fluorescent dyes, electron-dense reagents, enzymes (as commonly used in an ELISA), biotin, dioxigenin, or haptens and proteins for which antisera or monoclonal antibodies are available.

Use of Modified RTK Ligands in Cancer Therapeutics

As described above, the abnormal expression (especially amplification) of RTKs is associated with the etiology of a number of cancers suggesting that RTK activation is associated with tumorigenesis. The modified ligands of the present invention may have a therapeutic use in the modulation or blocking of RTK activity in tumor cells. Thus, this invention provides for therapeutic compositions or medicaments comprising the analogs herein in combination with a pharmaceutically acceptable excipient wherein the amount of the analog is sufficient to provide a therapeutic effect.

In a therapeutic application, the modified RTK ligands of the present invention are embodied in pharmaceutical compositions intended for parenteral, topical, oral or local administration. Preferably, the pharmaceutical compositions are administered parenterally, e.g., intravenously, subcutaneously, intradermally, or intramuscularly. Thus, the invention provides compositions for parenteral administration which comprise a solution of the agents described above dissolved or suspended in an acceptable carrier, preferably an aqueous carrier. A variety of aqueous carriers may be used, e.g., water, buffered water, 0.4% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient and more preferably at a concentration of 25%–75%.

For aerosol administration, the modified RTK ligands are preferably supplied in finely divided form along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery.

In therapeutic applications, the modified ligands of the invention are administered to a patient in a therapeutically effective amount, herein defined as an amount sufficient to prevent tumor growth. Methods of assessing tumor growth are well known to those of skill in the art. Amounts effective for this use will depend on, e.g., the particular modified ligand, the manner of administration, the weight and general state of health of the patient, and the judgment of the prescribing physician. In general the amounts would range from 100 mg to 1 gram.

The following examples are provided by way of illustration only and not by way of limitation. Those of skill will readily recognize a variety of noncritical parameters which could be changed or modified to yield essentially similar results.

EXAMPLE 1

Chemical Synthesis and Purification of Modified RTK Ligands

A. Automated peptide synthesis of the modified RTK ligands of this invention was performed on a Milligen/Biosearch Model 9600 peptide synthesizer using the standard Fmoc-DIPCDI/HOBT protocols except that, in several instances, the coupling time for a specific residue was modified. The reaction was performed on a 0.4 mmol scale and the initial residue was derivatized through a hydroxymethylphenoxyacetic acid linker to a methyl benzhydrylamine polystyrene resin. This Fmoc-alanine-PAC support (0.33 mmol/g loading) was purchased from MilliGen/Biosearch.

Following synthesis of the modified RTK ligand, cleavage of the dried resin-bound peptide was accomplished by resuspending the resin in a solution of 90:5:3:2 (v/v)/ trifluoroacetic acid (TFA):thioanisole: 1,2-ethanedithiol:anisole (1.0 g/20 mL). The resulting slurry was gently shaken at room temperature for 3.5 h before being filtered and washed with TFA (4×5 mL). The combined filtrates were evaporated in vacuo. The residue was redissolved in TFA (7 mL) and diethyl ether (200 mL) was added dropwise with stirring. The resulting white ppt. was vigorously stirred for 15 min and filtered. The filter cake was washed with ether (4×), dissolved in 50% aq. ACN and lyophilized to afford a white powder.

The cleaved peptide was analyzed and purified by HPLC. Analytical HPLC (Vydac; $C_{18}$, 0.46×15 cm, 5 mm, 300A ) was carried out on a Waters system consisting of 2 Model 510 pumps connected to a Model 680 automated gradient controller. Column effluent was monitored at 220 nm by a Model 490 spectrophotometer and peak area was measured with a Model 745B Data Module. Preparative HPLC (Vydac; $C_{18}$, 5×25 cm, 15–20 mm, 300A ) was carried out on a Gilson system consisting of 2 Model 303 pumps equipped with extended flow heads (permitting a maximum flow rate of 99 mL/min) and connected to a Model 803C manometer module and a Model 811 mixer. Column effluent was monitored at 220 nm by a Holochrome Model spectrophotometer. Gradients were run using a binary solvent system consisting of water (A) and acetonitrile (B), both containing 0.05% TFA.

The synthetic RTK ligand was folded to its native disulfide bond configuration by converting the cysteines in the peptide to their corresponding S-sulfonates. In a typical reaction, 5 mg of reduced lyophilized peptide was dissolved in 159 uL of water and 81 uL of 1.5M Tris HCL, pH 8.8. The cysteines in the peptide were spontaneously oxidized to disulfides by allowing the solution to stand at room temperature for 90 min. Sulfitolysis was performed by adding 960 uL of 10M urea to this solution followed by 150 uL of 1M $Na_2SO_3$ and then 150 uL of 0.2M $Na_2S_4O_6$. The reaction mixture was kept at room temperature for 2 h, after which the solution was dialyzed versus 1M urea, 20 mM Tris HCI, pH 7.1. Excess reagents used in the sulfitolysis reaction were removed by desalting over G-25 or dialysis. S-sulfonated peptide at a concentration of 0.2–3 mg/mL was adjusted to pH 8.5–8.8. EDTA was added to a final concentration of 1 mM and folding was initiated by the addition of cysteine to a final concentration of 3 mM. Generally, the reaction was allowed to proceed from 16 h to 24 h. The solution was acidified by the addition of one-tenth volume of 10% TFA.

B. Using this procedure, modified RTK ligands of the following sequences were made:
1. Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1);
2. Ser-His-Thr-Gln-Phe-Cys-Phe-His-Gly-Thr-Ser-Cys-Val-Cys-His-Ser-Gly-Tyr-Val-Gly-Ala-Arg-Cys-Glu-His-Ala-Asp-Leu-Leu-Ala (SEQ ID NO: 2);
3. Ser-His-Thr-Gln-Phe-Cys-Phe-His-Gly-Thr-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 3);
4. Ser-His-Thr-Gln-Phe-Cys-Phe-His-Gly-Thr-Ser-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 4);
5. Ser-His-Thr-Gln-Phe-Cys-Phe-His-Gly-Thr-Ser-Pro-Asn-Cys-Val-Cys-His-Ser-Gly-Tyr-Val-Gly-Ala-Arg-Cys-Glu-His-Ala-Asp-Leu-Leu-Ala (SEQ ID NO: 5);
6. Lys-Glu-Lys-Thr-Phe-Cys-Val-Asn-Gly-Gly-Glu-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 8).

EXAMPLE 2

Assaying for Binding and Antagonistic Activity of a Modified RTK Ligand

In this experiment, a modified RTK ligand (Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1)) synthesized as described in Example 1, was assayed for its ability to inhibit binding of epidermal growth factor (EGF) to the EGF receptor using the method described by Kimball and Warren, *Biochim. Biophys. Acta.*, 771: 82–88 (1984) which is herein incorporated in full by reference.

Commercial mouse EGF (Collaborative Research, Inc., Waltham, Mass.) was purified according to the method of Kimbal and Warren. Id. The isolated EGF was radioiodinated with $^{125}$I (Amersham, Arlington Heights, ill.) to a specific activity of about 21.5 μCi/μg of protein as described by Greenwood et al. *Biochem. J.*, 89: 114–123 (1963) which is incorporated herein by reference. A-431 human epidermoid carcinoma cells (ATCC), which have a high density of EGF receptors, were grown to confluency in roller bottles. Cell membranes were subsequently obtained by hypotonic lysis using the method described by Thom, et al. *Biochem. J.*, 168: 187–194 (1977) which is incorporated herein by reference. The membranes were dispensed into 96-well polyvinylchloride plates (Dynatch, Arlington, Va.) at 2.5 μg membrane protein/well in 100 μL Dulbecco's phosphate-buffered saline. The plates were dried overnight at 37° C., sealed and then stored at 4° C. until required.

Prior to use, the dried cell membranes were washed 4 times with 150 μL binding buffer (Dulbecco's Modified Eagles Medium containing 1 mg of bovine serum albumin per mL and 50 mM 2-[bis(2-hydroxyethyl)amino]ethane, Ph 6.8) and then pre-incubated 30 minutes at 23° C. with 150 μL of binding buffer.

Binding was initiated by the addition of 100 μL of binding buffer containing 4 ng/mL of $^{125}$I-EGF with or without modified RTK ligand (Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1)). The mixtures were incubated with the immobilized membranes for 1 hour at 23° C. and then removed by aspiration. Wells were washed four times with 200 μL of fresh binding buffer, separated from the plate with a hot wire and deposited into test tubes which were placed into a scintillation counter to determine the amount of bound $^{125}$I-ligand. Nonspecific binding was determined by treating membranes with a 100-fold excess of unlabelled modified RTK ligand to saturate the receptor sites and measuring the residual activity. Percent inhibition of binding was calculated according to the following formula:

$$\% \text{ inhibition} = 100 - \left[ \frac{cpm \text{ bound } EGF - \text{nonspecific } cpm \text{ bound}}{cpm \text{ bound (no ligand)} - \text{nonspecific } cpm \text{ bound}} \right] \times 100$$

where cpm stands for counts per minute measured using the scintillation counter. At 100% inhibition, the modified RTK ligand binds all available RTKs, thus blocking potential binding sites for EGF. At 0% inhibition, the converse is true. The standard curve for this experiment is shown in FIG. 3.

EXAMPLE 3

Assaying for Agonistic Activity of a Modified RTK Ligand

A. Determination of [$^3$H]-Thymidine Uptake

A number of native RTK ligands act as potent mitogens in a variety of cells. Thus agonistic activity of a modified RTK ligand may be ascertained by exposing a target cell to the modified RTK ligand and assaying for increased metabolic activity. This is typically measured as an increase in tritiated thymidine uptake by the target cell.

NRK cells are plated in 60 mm culture dishes containing 5 mL of Dulbecco's medium plus 10% calf serum. When the cells become confluent, the medium is removed and the cell monolayers are washed twice with Hank's balanced salt solution. Five mL of Dulbecco's medium plus 1% calf serum are added to each dish and the cells are incubated for 48 hours. The modified RTK ligand is added to each culture dish in concentrations of 0.5, 1, 2, 5, 10, and 50 ng/mL respectively. Positive controls are provided by a similar treatment with a native ligand, while negative controls are provided by a treatment with no ligand. Twenty hours later 1 μCi/mL of [methyl-$^3$H]-thymidine is added. The cells are labeled for 4 hours. Labeling is stopped by treating the cells with cold trichloroacetic acid (TCA). The TCA is decanted off, the cells are washed again with cold TCA which is decanted off, and the radioactivity in the remaining cold TCA insoluble material is counted using a scintillation counter.

Thymidine uptake of cells treated with the modified RTK ligand is compared to the respective positive and negative controls. Agonistic activity is revealed by a significant increase in tritiated thymidine uptake by the modified RTK ligand treated cells relative to the negative control. The degree of activity is ascertained by comparison to the results obtained using the positive control (the native ligand).

B. Determination of Cell Proliferation Rate

Alternatively, the agonistic properties of a modified RTK ligand may be assayed by measuring the effect of the modified RTK ligand on the growth of a target cell. NRK cells are plated in 60 mm culture dishes containing Dulbecco's modified medium supplemented with 10% calf serum, 10% calf serum supplemented with a native ligand (e.g. EGF) and 10% calf serum supplemented with the modified RTK ligand (12.5 ng/mL). The culture is maintained for 10 to 21 days. The total cell count in duplicate culture dishes is determined with a Coulter Counter.

Mitogenic activity is determined by comparison of the final cell count in the treatment as compared with the controls. Relative mitogenic activity is determined by comparison of the modified RTK ligand treatment with the native RTK ligand treatment after subtracting out the controls. Where the modified RTK ligand is mitogenic, cells will proliferate either more rapidly or to a higher final concentration in the modified RTK ligand treatments as compared to the control treatments.

C. Induction of Precocious Eyelid Opening

Agonistic activity of a modified RTK ligand may be ascertained by assaying for biological properties known to be present in naturally occurring analogs of the ligand both in vivo and in vitro. EGF is known to induce precocious eyelid opening activity in newborn mice. Modified RTK ligands specific to EGF receptors with agonistic properties will also be expected to show similar activities.

Eyelid opening activity is assayed by subcutaneous injection of the modified RTK ligand into a newborn mouse as described by Cohen, *J. Biol. Chem.*, 237: 1555–1562 (1973) incorporated herein by reference. Newborn mice are treated with subcutaneous injections of the modified RTK ligand (1 μg/g per day or 0.25 μg/g per day). The time period to eyelid opening in the modified ligand treated mice is compared to neutral control mice (no ligand in the treatment) and positive control mice (injected with the native ligand). Premature eyelid opening indicates an agonistic activity.

EXAMPLE 4

Quantification of Erb Receptor Tyrosine Kinase on Cancer Cells

A purified modified RTK ligand as prepared above in Example 1 is radioiodinated with $^{125}$I (Amersham, Arlington Heights, ill.) to a specific activity of about 21.5 μCi/μg of protein as described by Greenwood et al. *Biochem. J.*, 89: 114–123 (1963) which is incorporated herein by reference. Human carcinoma cells are obtained by biopsy. The tissue is disrupted and cell membranes are subsequently obtained by hypotonic lysis using the method described by Thom, et al. *Biochem. J.*, 168: 187–194 (1977) which is incorporated herein by reference. The membranes are dispensed into 96-well polyvinylchloride plates (Dynatch, Arlington, Va.) at 2.5 μg membrane protein/well in 100 μL Dulbecco's phosphate-buffered saline. The plates are dried overnight at 37° C.

The dried cell membranes are washed 4 times with 150 μL binding buffer (Dulbecco's Modified Eagles Medium containing 1 mg of bovine serum albumin per mL and 50 mM 2-[bis(2-hydroxyethyl)amino]ethane, pH 6.8) and then pre-incubated 30 minutes at 23° C. with 150 μL of binding buffer.

Binding is initiated by the addition of 100 μL of binding buffer containing 4 ng/mL of $^{125}$I-ligand. Negative controls are provided by non-tumor cells. The mixtures are incubated with the immobilized membranes for 1 hour at 23° C. and then removed by aspiration. Wells are washed four times with 200 μL of fresh binding buffer, separated from the plate with a hot wire and deposited into test tubes to determine the amount of bound $^{125}$I-ligand. Nonspecific binding is determined by treating membranes with a 100-fold excess of unlabeled ligand to saturate the receptor sites and measuring the residual activity.

Specific binding is determined as the total counts per minute minus the counts per minute attributable to nonspecific binding. RTK amplification is determined as the difference between counts obtained from tumor cells and from non-tumor cells.

What is claimed is:

1. A modified ligand having specificity for a Class I receptor tyrosine kinase (RTK) and corresponding to a native RTK ligand having amino acids forming three cysteine linkages, said linkages numbered in ascending order with regard to the relative position of their first cysteine with respect to the amino terminus of the native RTK ligand:

wherein the first, second, and third cysteine linkages of the native RTK ligand define a domain A, a domain B and a domain C, and the three linkages comprise a first, a second, a third, a fourth, a fifth and a sixth cysteine, with the first linkage being between the first and third cysteines, the second linkage being between the second and fourth cysteines and the third linkage being between the fifth and sixth cysteines; where domain A is defined as the first cysteine, those amino acids situated between the first and the second cysteines, and the second cysteine; domain B is defined as those amino acids situated between the second and fourth cysteines; and domain C is defined as the fourth cysteine and those amino acids attached to the carboxy terminus of the fourth cysteine; and, wherein the modified RTK ligand has four cysteine amino acids forming two linkages between cysteines two and four, and five and six, respectively, and having two domains, $A_1$ and $C_1$ corresponding to domains A and C of the native RTK ligand, wherein domain $A_1$ consists essentially of the biologically active amino acid sequences of the domain A of a native RTK ligand; and, wherein domain $C_1$ consists essentially of the biologically active amino acid sequences of the domain C of a native RTK ligand, wherein cysteine two, which is the carboxy terminus of domain $A_1$, and cysteine four, which is the amino terminus of domain $C_1$, are connected by a peptide bridge comprising a prebridge subdomain and a bridge subdomain, and where, within the peptide bridge, there is a β-turn corresponding to the β-turn present within domain B of the native RTK ligand, wherein the modified RTK ligand consists of the formula:

$$X1\text{-}X2_A\text{-}X2_B\text{-}X3$$

wherein X1 is domain $A_1$ and consists of amino acid residues $AA_1$-1 through $AA_1$-6, and where
- $AA_1$-1 is Ser;
- $AA_1$-2 is His;
- $AA_1$-3 is Thr;
- $AA_1$-4 is Gln;
- $AA_1$-5 is Phe;
- $AA_1$-6 is Cys; and wherein $X2_A$ and $X2_B$ taken together comprise the peptide bridge domain and wherein $X2_A$ is the prebridge subdomain and consists of amino acid residues $AA_{2A}$-1 through $AA_{2A}$-5, and where
- $AA_{2A}$-1 is Phe;
- $AA_{2A}$-2 is His;
- $AA_{2A}$-3 is Gly;
- $AA_{2A}$-4 is Thr; and
- $AA_{2A}$-5 is a peptide bond; and wherein $X2_B$ is the bridge subdomain and consists of 1 to 3 amino acid residues ($AA_{2B}$-1, $AA_{2B}$-2, $AA_{2B}$-3) and wherein, if $X2_B$ is one amino acid residue,
- $AA_{2B}$-1 is Gly or Ser;

wherein, if $X2_B$ is two amino acid residues,
- $AA_{2B}$-1 is Asp, Ser, Thr, or Pro and $AA_{2B}$-2 is Asp, Ser, Asn, or Arg; or
- $AA_{2B}$-1 is Pro and $AA_{2B}$-2 is Gly or Asn; or
- $AA_{2B}$-1 is Gly, Asn or Asp and $AA_{2B}$-2 is Gly; or
- $AA_{2B}$-1 is Gly and $AA_{2B}$-2 is Ser, Glu, Thr, Asn, Ala, Gly, Asp, or Lys; and wherein, if $X2_B$ is three amino acid residues,
- $AA_{2B}$-1 is any amino acid and
- $AA_{2B}$-2 is Asp, Ser, Thr, or Pro and $AA_{2B}$-3 is Asp, Ser, Asn, or Arg; or,
- $AA_{2B}$-2 is Pro and $AA_{2B}$-3 is Gly or Asn; or,
- $AA_{2B}$-2 is Gly, Asn, or Asp and $AA_{2B}$-3 is Gly; or
- $AA_{2B}$-2 is Gly and $AA_{2B}$-3 is Ser, Glu, Thr, Asn, Ala, Gly, Asp, or Lys; and wherein X3 is domain $C_1$ and consists of amino acid residues $AA_3$-1 through $AA_3$-19, and where
- $AA_3$-1 is Cys;
- $AA_3$-2 is Val;
- $AA_3$-3 is Cys;
- $AA_3$-4 is His;
- $AA_3$-5 is Ser;
- $AA_3$-6 is Gly;
- $AA_3$-7 is Tyr;
- $AA_3$-8 is Val:
- $AA_3$-9 is Gly;
- $AA_3$-10 is Ala;
- $AA_3$-11 is Arg;
- $AA_3$-12 is Cys;
- $AA_3$-13 is Glu;
- $AA_3$-14 is His;
- $AA_3$-15 is Ala;
- $AA_3$-16 is Asp;
- $AA_3$-17 is Leu;
- $AA_3$-18 is Leu; and
- $AA_3$-19 is Ala; and wherein said RTK is the EGF receptor.

2. The ligand of claim 1, wherein $X2_B$ is one residue where $AA_{2B}$-1 is Gly, and said ligand has the sequence:
Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1).

3. The ligand of claim 1, wherein $X2_B$ is one residue where $AA_{2B}$-1 is Ser, and said ligand has the sequence:
Ser-His-Thr-Gln-Phe-Cys-Phe-His-Gly-Thr-Ser-Cys-Val-Cys-His-Ser-Gly-Tyr-Val-Gly-Ala-Arg-Cys-Glu-His-Ala-Asp-Leu-Leu-Ala (SEQ ID NO: 2).

4. The ligand of claim 1, wherein $X2_B$ is two residues where $AA_{2B}$-1 is Pro and $AA_{2B}$-2 is Gly, and said ligand has the sequence:
Ser-His-Thr-Gln-Phe-Cys-Phe-His-Gly-Thr-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 3).

5. The ligand of claim 1, wherein $X2_B$ is three residues where $AA_{2B}$-1 is Ser, $AA_{2B}$-2 is Pro, and $AA_{2B}$-3 is Gly, and said ligand has the sequence:
Ser-His-Thr-Gln-Phe-Cys-Phe-His-Gly-Thr-Ser-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 4).

6. The ligand of claim 1, wherein $X2_B$ is three residues where $AA_{2B}$-1 is Ser, $AA_{2B}$-2 is Pro, and $AA_{2B}$-3 is Asn, and said ligand has the sequence:
Ser-His-Thr-Gln-Phe-Cys-Phe-His-Gly-Thr-Ser-Pro-Asn-Cys-Val-Cys-His-Ser-Gly-Tyr-Val-Gly-Ala-Arg-Cys-Glu-His-Ala-Asp-Leu-Leu-Ala (SEQ ID NO: 5).

7. A modified ligand having specificity for a Class I receptor tyrosine kinase (RTK) and corresponding to a native RTK ligand having amino acids forming three cysteine linkages, said linkages numbered in ascending order with regard to the relative position of their first cysteine with respect to the amino terminus of the native RTK ligand:

wherein the first, second, and third cysteine linkages of the native RTK ligand define a domain A, a domain B and a domain C, and the three linkages comprise a first, a second, a third, a fourth, a fifth and a sixth cysteine, with the first linkage being between the first and third cysteines, the second linkage being between the second and fourth cysteines and the third linkage being between the fifth and sixth cysteines; where domain A is defined as the first cysteine, those amino acids situated between the first and the second cysteines, and the second cysteine; domain B is defined as those amino acids situated between the second and fourth cysteines; and domain C is defined as the fourth cysteine and those amino acids attached to the carboxy terminus of the fourth cysteine; and, wherein the modified RTK ligand has four cysteine amino acids forming two linkages between cysteines two and four, and five and six, respectively, and having two domains, $A_1$ and $C_1$ corresponding to domains A and C of the native RTK ligand, wherein domain $A_1$ consists essentially of the biologically active amino acid sequences of the domain A of a native RTK ligand; and, wherein domain $C_1$ consists essentially of the biologically active amino acid sequences of the domain C of a native RTK ligand, wherein cysteine two, which is the carboxy terminus of domain $A_1$, and cysteine four, which is the amino terminus of domain $C_1$, are connected by a peptide bridge comprising a prebridge subdomain and a bridge subdomain, and where, within the peptide bridge, there is a β-turn corresponding to the β-turn present within domain B of the native RTK ligand, wherein the modified RTK ligand consists of the formula:

X1-X2$_A$-X2$_B$-X3 wherein X1 is domain $A_1$ and consists of amino acid residues $AA_1$-1 through $AA_1$-6, and where
$AA_1$-1 is Lys;
$AA_1$-2 is Glu;
$AA_1$-3 is Lys;
$AA_1$-4 is Thr;
$AA_1$-5 is Phe;
$AA_1$-6 is Cys; and
wherein $X2_A$ and $X2_B$ taken together comprise the peptide bridge domain and wherein $X2_A$ is the prebridge subdomain and consists of amino acid residues $AA_{2A}$-1 through $AA_{2A}$-5, and where
$AA_{2A}$-1 is Val;
$AA_{2A}$-2 is Asn;
$AA_{2A}$-3 is Gly;
$AA_{2A}$-4 is Gly;
$AA_{2A}$-5 is Glu; and
wherein $X2_B$ is the bridge subdomain and consists of 1 to 3 amino acid residues ($AA_{2B}$-1, $AA_{2B}$-2, $AA_{2B}$-3) and
wherein, if $X2_B$ is one amino acid residue,
$AA_{2B}$-1 is Gly or Ser;
wherein, if $X2_B$ is two amino acid residues,
$AA_{2B}$-1 is Asp, Ser, Thr, or Pro and $AA_{2B}$-2 is Asp, Ser, Asn, or Arg; or
$AA_{2B}$-1 is Pro and $AA_{2B}$-2 is Gly or Asn; or
$AA_{2B}$-1 is Gly, Asn or Asp and $AA_{2B}$-2 is Gly; or
$AA_{2B}$-1 is Gly and $AA_{2B}$-2 is Ser, Glu, Thr, Asn, Ala, Gly, Asp, or Lys; and
wherein, if $X2_B$ is three amino acid residues,
$AA_{2B}$-1 is any amino acid and
$AA_{2B}$-2 is Asp, Ser, Thr, or Pro and $AA_{2B}$-3 is Asp, Ser, Asn, or Arg; or,
$AA_{2B}$-2 is Pro and $AA_{2B}$-3 is Gly or Asn; or,
$AA_{2B}$-2 is Gly, Asn, or Asp and $AA_{2B}$-3 is Gly; or
$AA_{2B}$-2 is Gly and $AA_{2B}$-3 is Ser, Glu, Thr, Asn, Ala, Gly, Asp, or Lys; and
wherein X3 is domain $C_1$ and consists of amino acid residues AA3-1 through $AA_3$-19, and where
$AA_3$-1 is Cys;
$AA_3$-2 is Lys;
$AA_3$-3 is Cys;
$AA_3$-4 is Gln;
$AA_3$-5 is Pro;
$AA_3$-6 is Gly;
$AA_3$-7 is Phe:
$AA_3$-8 is Thr;
$AA_3$-9 is Gly;
$AA_3$-10 is Ala;
$AA_3$-11 is Arg;
$AA_3$-12 is Cys;
$AA_3$-13 is Thr;
$AA_3$-14 is Glu;
$AA_3$-15 is Asn;
$AA_3$-16 is Val;
$AA_3$-17 is Pro;
$AA_3$-18 is Met; and
$AA_3$-19 is Lys; and
wherein said RTK is an RTK receptor other than the EGF receptor.

8. The ligand of claim 7, wherein $X2_B$ is one residue where $AA_{2B}$-1 is Gly, and said ligand has the sequence:
Lys-Glu-Lys-Thr-Phe-Cys-Val-Asn-Gly-Gly-Glu-Gly-Cys-Lys-Cys-Gln-Pro-Gly-Phe-Thr-Gly-Ala-Arg-Cys-Thr-Glu-Asn-Val-Pro-Met-Lys (SEQ ID NO: 6).

9. The ligand of claim 7, wherein $X2_B$ is one residue where $AA_{2B}$-1 is Ser, and said ligand has the sequence:
Lys-Glu-Lys-Thr-Phe-Cys-Val-Asn-Gly-Gly-Glu-Ser-Cys-Lys-Cys-Gln-Pro-Gly-Phe-Thr-Gly-Ala-Arg-Cys-Thr-Glu-Asn-Val-Pro-Met-Lys (SEQ ID NO: 7).

10. The ligand of claim 7, wherein $X2_B$ is two residues where $AA_{2B}$-1 is Pro and $AA_{2B}$-2 is Gly, and said ligand has the sequence:
Lys-Glu-Lys-Thr-Phe-Cys-Val-Asn-Gly-Gly-Glu-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 8).

11. The ligand of claim 7, wherein $X2_B$ is three residues where $AA_{2B}$-1 is Ser, $AA_{2B}$-2 is Pro, and $AA_{2B}$-3 is Gly, and said ligand has the sequence:
Lys-Glu-Lys-Thr-Phe-Cys-Val-Asn-Gly-Gly-Glu-Ser-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO; 9).

12. The ligand of claim 7, wherein $X2_B$ is three residues where $AA_{2B}$-1 is Ser, $AA_{2B}$-2 is Pro, and $AA_{2B}$-3 is Asn, and said ligand has the sequence:
Lys-Glu-Lys-Thr-Phe-Cys-Val-Asn-Gly-Gly-Glu-Ser-Pro-Asn-Cys-Lys-Cys-Gln-Pro-Gly-Phe-Thr-Gly-Ala-Arg-Cys-Thr-Glu-Asn-Val-Pro-Met-Lys (SEQ ID NO: 10).

13. A method for quantifying the presence of RTKs on a human cell comprising the following steps:
(a) contacting said cell with the modified RTK ligand of claim 1 or claim 7, and
(b) detecting the amount of said modified RTK ligand bound to said cell.

14. The method of claim 13, wherein said ligand is the ligand of claim 1 and has the sequence:
Ser-His-Thr-Gln-Phe-Cys-Phe-His-Gly-Thr-Gly-Cys-Val-Cys-His-Ser-Gly-Tyr-Val-Gly-Ala-Arg-Cys-Glu-His-Ala-Asp-Leu-Leu-Ala (SEQ ID NO: 1).

15. The method of claim 13, wherein said ligand is the ligand of claim 1 and has the sequence:
Ser-His-Thr-Gln-Phe-Cys-Phe-His-Gly-Thr-Ser-Cys-Val-Cys-His-Ser-Gly-Tyr-Val-Gly-Ala-Arg-Cys-Glu-His-Ala-Asp-Leu-Leu-Aia (SEQ ID NO: 2).

16. The method of claim 13, wherein said ligand is the ligand of claim 1 and has the sequence:
Ser-His-Thr-Gln-Phe-Cys-Phe-His-Gly-Thr-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 3).

17. The method of claim 13, wherein said ligand is the ligand of claim 1 and has the sequence:
Ser-His-Thr-Gln-Phe-Cys-Phe-His-Gly-Thr-Ser-Pro-Gly-Cys-Val-Cys-His-Ser-Gly-Tyr-Val-Gly-Ala-Arg-Cys-Glu-His-Ala-Asp-Leu-Leu-Ala (SEQ ID NO: 4).

18. The method of claim 13, wherein said ligand is the ligand of claim 1 and has the sequence:
Ser-His-Thr-Gln-Phe-Cys-Phe-His-Gly-Thr-Ser-Pro-Asn-Cys-Val-Cys-His-Ser-Gly-Tyr-Val-Gly-Ala-Arg-Cys-Glu-His-Ala-Asp-Leu-Leu-Ala (SEQ ID NO: 5).

19. The method of claim 13, wherein said ligand is the ligand of claim 7 and has the sequence;
Lys-Glu-Lys-Thr-Phe-Cys-Val-Asn-Gly-Gly-Glu-Gly-Cys-Lys-Cys-Gln-Pro-Gly-Phe-Thr-Gly-Ala-Arg-Cys-Thr-Glu-Asn-Val-Pro-Met-Lys (SEQ ID NO: 6).

20. The method of claim 13, wherein said ligand is the ligand of claim 7 and has the sequence:
Lys-Glu-Lys-Thr-Phe-Cys-Val-Asn-Gly-Gly-Glu-Ser-Cys-Lys-Cys-Gln-Pro-Gly-PheThr-Gly-Ala-Arg-Cys-Thr-Glu-Asn-Val-Pro-Met-Lys (SEQ ID NO: 7).

21. The method of claim 13, wherein said ligand is the ligand of claim 7 and has the sequence:

Lys-Glu-Lys-Thr-Pho-Cys-Val-Asn-Gly-Gly-Glu-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 8).

22. The method of claim 13, wherein said ligand is the ligand of claim 7 and has the sequence:

Lys-Glu-Lys-Thr-Phe-Cys-Val-Asn-Gly-Gly-Glu-Ser-Pro-Gly-Cys-Lys-Cys-Gln-Pro-Gly-Phe-Thr-Gly-Ala-Arg-Cys-Thr-Glu-Asn-Val-Pro-Met-Lys (SEQ ID NO: 9).

23. The method of claim 13, wherein said ligand is the ligand of claim 7 and has the sequence:

Lys-Glu-Lys-Thr-Phe-Cys-Val-Asn-Gly-Gly-Glu-Ser-Pro-Asn-Cys-Lys-Cys-Gln-Pro-Gly-Phe-Thr-Gly-Ala-Arg-Cys-Thr-Glu-Asn-Val-Pro-Met-Lys (SEQ ID NO: 10).

24. A method for treating malignancy which comprises administering to a patient in need thereof a therapeutically effective amount of the modified RTK ligand of claim 1 or claim 7.

25. A pharmaceutical composition consisting essentially of the modified RTK ligand of claim 1 or claim 7 and a pharmaceutically acceptable excipient.

* * * * *